(12) United States Patent
Ezura et al.

(10) Patent No.: US 10,745,710 B2
(45) Date of Patent: Aug. 18, 2020

(54) PLANT HAVING MUTANT CYCLIN F-BOX GENE

(71) Applicant: UNIVERSITY OF TSUKUBA, Tsukuba-shi, Ibaraki (JP)

(72) Inventors: Hiroshi Ezura, Tsukuba (JP); Tohru Ariizumi, Tsukuba (JP); Jun-ichiro Masuda, Tsukuba (JP); Yoshihiro Okabe, Tsukuba (JP)

(73) Assignee: UNIVERSITY OF TSUKUBA, Tsukuba-Shi, Igaraki (JP)

( * ) Notice: Subject to any disclaimer, the term of this patent is extended or adjusted under 35 U.S.C. 154(b) by 0 days.

(21) Appl. No.: 15/750,386

(22) PCT Filed: Aug. 5, 2016

(86) PCT No.: PCT/JP2016/073164
§ 371 (c)(1),
(2) Date: Feb. 5, 2018

(87) PCT Pub. No.: WO2017/022859
PCT Pub. Date: Feb. 9, 2017

(65) Prior Publication Data
US 2019/0110420 A1 Apr. 18, 2019

(30) Foreign Application Priority Data

Aug. 6, 2015 (JP) ................. 2015-156140

(51) Int. Cl.
| | | |
|---|---|---|
| *A01H 5/08* | (2018.01) | |
| *A01H 6/82* | (2018.01) | |
| *A01H 3/04* | (2006.01) | |
| *C12N 15/82* | (2006.01) | |
| *A01H 1/02* | (2006.01) | |
| *A01H 1/04* | (2006.01) | |

(52) U.S. Cl.
CPC ........... *C12N 15/8246* (2013.01); *A01H 3/04* (2013.01); *A01H 5/08* (2013.01); *A01H 6/825* (2018.05); *C12N 15/8261* (2013.01); *A01H 1/02* (2013.01); *A01H 1/04* (2013.01)

(58) Field of Classification Search
None
See application file for complete search history.

(56) References Cited

U.S. PATENT DOCUMENTS

| 9,474,222 B2 * | 10/2016 | Van Heusden | .......... A01H 1/02 |
|---|---|---|---|
| 2010/0242141 A1 | 9/2010 | Ogawa | |
| 2011/0165312 A1 | 7/2011 | Kanno | |

FOREIGN PATENT DOCUMENTS

| EP | 3 095 863 | 11/2016 |
|---|---|---|
| JP | 2001-510685 A | 8/2001 |
| JP | 2004-331507 A | 11/2004 |
| JP | 2012-65601 A | 4/2012 |
| JP | 2012-100595 A | 5/2012 |
| JP | 2012-161289 A | 8/2012 |
| JP | 2012-530503 A | 12/2012 |
| WO | WO 1999/04621 A1 | 2/1999 |
| WO | WO 99/21411 | 5/1999 |
| WO | WO 2005/094557 A1 | 10/2005 |
| WO | WO 2009/005343 A1 | 1/2009 |
| WO | WO 2009/063806 A1 | 5/2009 |
| WO | WO 2010/021330 A1 | 2/2010 |
| WO | WO 2010/149628 A1 | 12/2010 |
| WO | WO 2015/108185 A1 | 7/2015 |

OTHER PUBLICATIONS

Predicted: F-Box/Kelch-Repeat Protein At3g61590 [Solanum Lycopersicum], XP_004229966, NCBI, Nov. 19, 2014 (Year: 2014).*
Skolnick J. et al. (From genes to protein structure and function: novel applications of computational approaches in the genomic era. Trends Biotechnl. Jan. 2000;18(1):34-9. Review. (Year: 2000).*
Whisstock J.C. et al. Prediction of protein function from protein sequence and structure. Q Rev Biophys. Aug. 2003;36(3):307-40. Review. (Year: 2003).*
Sjolander Phylogenomic inference of protein molecular function: advances and challenges. Bioinformatics. Jan. 22, 2004;20(2):170-9 (Year: 2004).*
Communication pursuant to Rule 164(1) EPC received in the corresponding European Application No. 16833138.7 dated Apr. 9, 2019, accompanying Supplementary Partial European Search Report (date of completion of the search: Mar. 27, 2019), and Japanese associate's reporting letter dated Jun. 4, 2019.
Ren, Z., et al., "The auxin receptor homologue in Solarium lycopersicum stimulates tomato fruit set and leaf morphogenesis," *Journal of Experimental Botany*, 62(8):2815-2826 (2011).
Database GenBank—Nucleotide [Online] NCBI, "Solanum lycopersicum F-box/kelch-repeat protein At3g61590 (LOC101247559), mRNA," XP-002790103, Database accession No. XM_004229918.2 (Abstract) (Nov. 19, 2014).
Boycheva, I., et al. "Cyclin-like F-box protein plays a role in growth and development of the three model species Medicago truncatula, Lotus japonicus, and *Arabidopsis thaliana*," *Research and Reports in Biology*, 6:117-130 (2015).

(Continued)

*Primary Examiner* — Cynthia E Collins

(74) *Attorney, Agent, or Firm* — Brinks Gilson & Lione

(57) ABSTRACT

The present invention relates to a plant having an improved sugar content in fruit compared with its wild type plant, which has a mutant cyclin F-box gene comprising a nucleotide mutation that causes a non-conservative amino acid substitution in the cyclin F-box protein. The present invention also relates to a parthenocarpic plant having a mutant cyclin F-box gene comprising a nucleotide mutation that causes a non-conservative amino acid substitution in the cyclin F-box protein.

9 Claims, 11 Drawing Sheets

Specification includes a Sequence Listing.

(56) References Cited

OTHER PUBLICATIONS

Predicted: F-Box/Kelch-Repeat Protein At3g61590 [Solanum Lycopersicum], Nov. 11, 2014, retrieved from the internet on Sep. 21, 2016 at https://www.ncbi.nlm.nih.gov/protein/XP_004229966, 1 page.
International Search Report, and English language translation thereof, in corresponding International Application No. PCT/JP2016/073164, dated Nov. 1, 2016, 7 pages.
Reporting Letter received from Japanese associate dated Oct. 9, 2019 and Extended European Search Report dated Jul. 24, 2019 received in corresponding European Application No. EP 16833138.7.
Database GenBank—Nucleotide [Online] NCBI; "Predicted: Nicotiana sylvestris F-box/kelch-repeat protein At3g61590 (LOC104242766), mRNA," XP002792807, Database accession No. XM_009797847.1, 2 pages, Oct. 21, 2014.
Database EMBL [Online] "Solanum lycopersicum cDNA, clone: LEFL1085DD11, HTC in leaf," XP002792703, retrieved from EBI accession No. EMBL: AK247660, Database accession No. AK247660, *sequence,* 2 pages, Jun. 4, 2007.

* cited by examiner

SEQUENCE LISTING

```
<160> NUMBER OF SEQ ID NOS: 26

<210> SEQ ID NO 1
<211> LENGTH: 1215
<212> TYPE: DNA
<213> ORGANISM: Solanum lycopersicum
<220> FEATURE:
<221> NAME/KEY: CDS
<222> LOCATION: (1)..(1215)
<220> FEATURE:
<223> OTHER INFORMATION: CDS sequence encoding wild-type cyclin F-box
      protein

<400> SEQUENCE: 1 atg gaa gaa acc tct tgg gtc agt cat tgc cct gat tac gtt gta cca        48
Met Glu Glu Thr Ser Trp Val Ser His Cys Pro Asp Tyr Val Val Pro
1               5                   10                  15 gac atg gtt gag ttt gat tca ttt tca gag ctt aat gat gaa gaa aat        96
Asp Met Val Glu Phe Asp Ser Phe Ser Glu Leu Asn Asp Glu Glu Asn
            20                  25                  30 aga gag gct tcc tca gtt cct gtg gat ttg ata ctg cct gat gat tta       144
Arg Glu Ala Ser Ser Val Pro Val Asp Leu Ile Leu Pro Asp Asp Leu
        35                  40                  45 ctg gaa cgc ata ctg gcc tat ctt ccc att gcc agc att ttt agg gca       192
Leu Glu Arg Ile Leu Ala Tyr Leu Pro Ile Ala Ser Ile Phe Arg Ala
    50                  55                  60 agt tgt gtg tgt aaa aga tgg tgt gag ata gtg aat tca aga agg ttt       240
Ser Cys Val Cys Lys Arg Trp Cys Glu Ile Val Asn Ser Arg Arg Phe
```

-continued

| | | | | | | | | | | | | | | | | |
|---|---|---|---|---|---|---|---|---|---|---|---|---|---|---|---|---|
| | | 65 | | | | 70 | | | | 75 | | | | 80 | | |
| tta | tgg | aac | ttc | tct | cag | gtg | ctg | tct | caa | aaa | ccg | tgg | tac | ttt | atg | 288 |
| Leu | Trp | Asn | Phe | Ser | Gln | Val | Leu | Ser | Gln | Lys | Pro | Trp | Tyr | Phe | Met | |
| | | | | 85 | | | | | 90 | | | | | 95 | | |
| ttc | aca | agc | tca | gag | gag | cca | gtt | ggt | tat | gcc | tat | gat | cct | tcc | ctt | 336 |
| Phe | Thr | Ser | Ser | Glu | Glu | Pro | Val | Gly | Tyr | Ala | Tyr | Asp | Pro | Ser | Leu | |
| | | | 100 | | | | | 105 | | | | | 110 | | | |
| cga | aaa | tgg | tat | agt | att | gac | ctc | cct | tgc | att | cag | aca | tca | aat | tgg | 384 |
| Arg | Lys | Trp | Tyr | Ser | Ile | Asp | Leu | Pro | Cys | Ile | Gln | Thr | Ser | Asn | Trp | |
| | | 115 | | | | | 120 | | | | | 125 | | | | |
| ttc | att | gct | tct | tca | tgt | gga | tta | gtt | tgc | atc | atg | gac | aat | gac | agt | 432 |
| Phe | Ile | Ala | Ser | Ser | Cys | Gly | Leu | Val | Cys | Ile | Met | Asp | Asn | Asp | Ser | |
| 130 | | | | | 135 | | | | | 140 | | | | | | |
| aga | agc | gaa | cta | tat | gtt | tgt | aac | cca | ata | acc | aaa | tgc | agc | aag | aac | 480 |
| Arg | Ser | Glu | Leu | Tyr | Val | Cys | Asn | Pro | Ile | Thr | Lys | Cys | Ser | Lys | Asn | |
| 145 | | | | | 150 | | | | | 155 | | | | | 160 | |
| ctt | cag | gag | cct | cct | ggt | ctc | aag | ttt | tct | gat | tac | agt | gca | ttg | gct | 528 |
| Leu | Gln | Glu | Pro | Pro | Gly | Leu | Lys | Phe | Ser | Asp | Tyr | Ser | Ala | Leu | Ala | |
| | | | | 165 | | | | | 170 | | | | | 175 | | |
| atc | tgt | gca | aac | atg | aaa | act | tct | tgt | tac | agt | gtc | gcc | att | gtt | aaa | 576 |
| Ile | Cys | Ala | Asn | Met | Lys | Thr | Ser | Cys | Tyr | Ser | Val | Ala | Ile | Val | Lys | |
| | | | 180 | | | | | 185 | | | | | 190 | | | |
| tct | aag | caa | gta | cct | ggt | aac | ttc | tat | cag | tgg | gat | ctc | tca | atc | cac | 624 |
| Ser | Lys | Gln | Val | Pro | Gly | Asn | Phe | Tyr | Gln | Trp | Asp | Leu | Ser | Ile | His | |
| | | 195 | | | | | 200 | | | | | 205 | | | | |
| ata | tat | gat | tct | gga | aca | atg | aag | tgg | ttg | acc | cct | ttg | aca | gag | gtt | 672 |
| Ile | Tyr | Asp | Ser | Gly | Thr | Met | Lys | Trp | Leu | Thr | Pro | Leu | Thr | Glu | Val | |
| 210 | | | | | 215 | | | | | 220 | | | | | | |
| cta | aca | ggc | tgg | aga | ggt | ggg | gat | gaa | agt | gtc | atc | tgt | gat | ggt | gtt | 720 |
| Leu | Thr | Gly | Trp | Arg | Gly | Gly | Asp | Glu | Ser | Val | Ile | Cys | Asp | Gly | Val | |
| 225 | | | | | 230 | | | | | 235 | | | | | 240 | |
| ttg | tac | ttc | ctg | atc | tat | gca | act | gga | ggt | ggt | gga | cta | gaa | agt | cgt | 768 |
| Leu | Tyr | Phe | Leu | Ile | Tyr | Ala | Thr | Gly | Gly | Gly | Gly | Leu | Glu | Ser | Arg | |
| | | | | 245 | | | | | 250 | | | | | 255 | | |
| cat | ggt | ctg | atc | act | tac | aac | ctc | tca | agc | aga | tca | tcc | cat | tgt | tcg | 816 |
| His | Gly | Leu | Ile | Thr | Tyr | Asn | Leu | Ser | Ser | Arg | Ser | Ser | His | Cys | Ser | |
| | | | 260 | | | | | 265 | | | | | 270 | | | |
| tta | ata | aag | act | ttc | att | ccc | gtg | cca | tgt | tct | cta | aca | tgt | ggt | cga | 864 |
| Leu | Ile | Lys | Thr | Phe | Ile | Pro | Val | Pro | Cys | Ser | Leu | Thr | Cys | Gly | Arg | |
| | | 275 | | | | | 280 | | | | | 285 | | | | |
| ttg | atg | aac | ctc | aag | gag | aag | tta | gta | atg | gtg | gga | ggg | att | ggg | aaa | 912 |
| Leu | Met | Asn | Leu | Lys | Glu | Lys | Leu | Val | Met | Val | Gly | Gly | Ile | Gly | Lys | |
| | 290 | | | | | 295 | | | | | 300 | | | | | |
| cca | gac | cgt | cct | gac | ata | att | aag | ggg | att | ggc | ata | tgg | gca | ctt | cag | 960 |
| Pro | Asp | Arg | Pro | Asp | Ile | Ile | Lys | Gly | Ile | Gly | Ile | Trp | Ala | Leu | Gln | |
| 305 | | | | | 310 | | | | | 315 | | | | | 320 | |
| ggg | aca | gaa | tgg | caa | gaa | att | gcc | cgc | atg | cca | cac | aag | tat | ttt | caa | 1008 |
| Gly | Thr | Glu | Trp | Gln | Glu | Ile | Ala | Arg | Met | Pro | His | Lys | Tyr | Phe | Gln | |
| | | | | 325 | | | | | 330 | | | | | 335 | | |
| ggt | ttt | ggg | gaa | ttc | gat | gat | gtt | ttt | gcc | agc | agt | ggc | act | gat | gat | 1056 |
| Gly | Phe | Gly | Glu | Phe | Asp | Asp | Val | Phe | Ala | Ser | Ser | Gly | Thr | Asp | Asp | |
| | | | 340 | | | | | 345 | | | | | 350 | | | |
| ctc | ata | tac | att | cag | agt | tat | gga | gct | cct | gcc | ctt | ctt | gtt | ttt | gac | 1104 |
| Leu | Ile | Tyr | Ile | Gln | Ser | Tyr | Gly | Ala | Pro | Ala | Leu | Leu | Val | Phe | Asp | |
| | | 355 | | | | | 360 | | | | | 365 | | | | |
| gtg | aac | cag | aaa | cag | tgg | agg | tgg | tca | cag | aaa | tgt | cca | gtg | aca | aag | 1152 |
| Val | Asn | Gln | Lys | Gln | Trp | Arg | Trp | Ser | Gln | Lys | Cys | Pro | Val | Thr | Lys | |
| 370 | | | | | 375 | | | | | 380 | | | | | | |
| agg | ttt | ccc | ctt | cag | ctc | ttt | act | ggt | ttc | tgc | ttc | gag | cca | agg | ctt | 1200 |

```
Arg Phe Pro Leu Gln Leu Phe Thr Gly Phe Cys Phe Glu Pro Arg Leu
385                 390                 395                 400 gag atg tct ccc tga                                              1215
Glu Met Ser Pro
```

<210> SEQ ID NO 2
<211> LENGTH: 404
<212> TYPE: PRT
<213> ORGANISM: Solanum lycopersicum
<220> FEATURE:
<223> OTHER INFORMATION: Amino acid sequence of wild-type cyclin F-box
      protein

<400> SEQUENCE: 2

```
Met Glu Glu Thr Ser Trp Val Ser His Cys Pro Asp Tyr Val Val Pro
1               5                   10                  15

Asp Met Val Glu Phe Asp Ser Phe Ser Glu Leu Asn Asp Glu Glu Asn
            20                  25                  30

Arg Glu Ala Ser Ser Val Pro Val Asp Leu Ile Leu Pro Asp Asp Leu
        35                  40                  45

Leu Glu Arg Ile Leu Ala Tyr Leu Pro Ile Ala Ser Ile Phe Arg Ala
    50                  55                  60

Ser Cys Val Cys Lys Arg Trp Cys Glu Ile Val Asn Ser Arg Arg Phe
65                  70                  75                  80

Leu Trp Asn Phe Ser Gln Val Leu Ser Gln Lys Pro Trp Tyr Phe Met
                85                  90                  95

Phe Thr Ser Ser Glu Glu Pro Val Gly Tyr Ala Tyr Asp Pro Ser Leu
            100                 105                 110

Arg Lys Trp Tyr Ser Ile Asp Leu Pro Cys Ile Gln Thr Ser Asn Trp
        115                 120                 125

Phe Ile Ala Ser Ser Cys Gly Leu Val Cys Ile Met Asp Asn Asp Ser
    130                 135                 140

Arg Ser Glu Leu Tyr Val Cys Asn Pro Ile Thr Lys Cys Ser Lys Asn
145                 150                 155                 160

Leu Gln Glu Pro Pro Gly Leu Lys Phe Ser Asp Tyr Ser Ala Leu Ala
                165                 170                 175

Ile Cys Ala Asn Met Lys Thr Ser Cys Tyr Ser Val Ala Ile Val Lys
            180                 185                 190

Ser Lys Gln Val Pro Gly Asn Phe Tyr Gln Trp Asp Leu Ser Ile His
        195                 200                 205

Ile Tyr Asp Ser Gly Thr Met Lys Trp Leu Thr Pro Leu Thr Glu Val
    210                 215                 220

Leu Thr Gly Trp Arg Gly Gly Asp Glu Ser Val Ile Cys Asp Gly Val
225                 230                 235                 240

Leu Tyr Phe Leu Ile Tyr Ala Thr Gly Gly Gly Gly Leu Glu Ser Arg
                245                 250                 255

His Gly Leu Ile Thr Tyr Asn Leu Ser Ser Arg Ser Ser His Cys Ser
            260                 265                 270

Leu Ile Lys Thr Phe Ile Pro Val Pro Cys Ser Leu Thr Cys Gly Arg
        275                 280                 285

Leu Met Asn Leu Lys Glu Lys Leu Val Met Val Gly Gly Ile Gly Lys
    290                 295                 300

Pro Asp Arg Pro Asp Ile Ile Lys Gly Ile Gly Ile Trp Ala Leu Gln
305                 310                 315                 320

Gly Thr Glu Trp Gln Glu Ile Ala Arg Met Pro His Lys Tyr Phe Gln
                325                 330                 335
```

```
Gly Phe Gly Glu Phe Asp Asp Val Phe Ala Ser Ser Gly Thr Asp Asp
            340                 345                 350

Leu Ile Tyr Ile Gln Ser Tyr Gly Ala Pro Ala Leu Leu Val Phe Asp
            355                 360                 365

Val Asn Gln Lys Gln Trp Arg Trp Ser Gln Lys Cys Pro Val Thr Lys
370                 375                 380

Arg Phe Pro Leu Gln Leu Phe Thr Gly Phe Cys Phe Glu Pro Arg Leu
385                 390                 395                 400

Glu Met Ser Pro

<210> SEQ ID NO 3
<211> LENGTH: 1215
<212> TYPE: DNA
<213> ORGANISM: Solanum lycopersicum
<220> FEATURE:
<221> NAME/KEY: CDS
<222> LOCATION: (1)..(1215)
<220> FEATURE:
<223> OTHER INFORMATION: CDS sequence encoding mutant cyclin F-box
      protein (from E8986)

<400> SEQUENCE: 3
```

| | | | | | | | | | | | | | | | | |
|---|---|---|---|---|---|---|---|---|---|---|---|---|---|---|---|---|
| atg | gaa | gaa | acc | tct | tgg | gtc | agt | cat | tgc | cct | gat | tac | gtt | gta | cca | 48 |
| Met | Glu | Glu | Thr | Ser | Trp | Val | Ser | His | Cys | Pro | Asp | Tyr | Val | Val | Pro | |
| 1 | | | | 5 | | | | | 10 | | | | | 15 | | |
| gac | atg | gtt | gag | ttt | gat | tca | ttt | tca | gag | ctt | aat | gat | gaa | gaa | aat | 96 |
| Asp | Met | Val | Glu | Phe | Asp | Ser | Phe | Ser | Glu | Leu | Asn | Asp | Glu | Glu | Asn | |
| | | | 20 | | | | | 25 | | | | | 30 | | | |
| aga | gag | gct | tcc | tca | gtt | cct | gtg | gat | ttg | ata | ctg | cct | gat | gat | tta | 144 |
| Arg | Glu | Ala | Ser | Ser | Val | Pro | Val | Asp | Leu | Ile | Leu | Pro | Asp | Asp | Leu | |
| | | 35 | | | | | 40 | | | | | 45 | | | | |
| ctg | gaa | cgc | ata | ctg | gcc | tat | ctt | ccc | att | gcc | agc | att | ttt | agg | gca | 192 |
| Leu | Glu | Arg | Ile | Leu | Ala | Tyr | Leu | Pro | Ile | Ala | Ser | Ile | Phe | Arg | Ala | |
| | 50 | | | | | 55 | | | | | 60 | | | | | |
| agt | tgt | gtg | tgt | aaa | aga | tgg | tgt | gag | ata | gtg | aat | tca | aga | agg | ttt | 240 |
| Ser | Cys | Val | Cys | Lys | Arg | Trp | Cys | Glu | Ile | Val | Asn | Ser | Arg | Arg | Phe | |
| 65 | | | | | 70 | | | | | 75 | | | | | 80 | |
| tta | tgg | aac | ttc | tct | cag | gtg | ctg | tct | caa | aaa | ccg | tgg | tac | ttt | atg | 288 |
| Leu | Trp | Asn | Phe | Ser | Gln | Val | Leu | Ser | Gln | Lys | Pro | Trp | Tyr | Phe | Met | |
| | | | | 85 | | | | | 90 | | | | | 95 | | |
| ttc | aca | agc | tca | gag | gag | cca | gtt | ggt | tat | gcc | tat | gat | cct | tcc | ctt | 336 |
| Phe | Thr | Ser | Ser | Glu | Glu | Pro | Val | Gly | Tyr | Ala | Tyr | Asp | Pro | Ser | Leu | |
| | | | 100 | | | | | 105 | | | | | 110 | | | |
| cga | aaa | tgg | tat | agt | att | gac | ctc | cct | tgc | att | cag | aca | tca | aat | tgg | 384 |
| Arg | Lys | Trp | Tyr | Ser | Ile | Asp | Leu | Pro | Cys | Ile | Gln | Thr | Ser | Asn | Trp | |
| | | 115 | | | | | 120 | | | | | 125 | | | | |
| ttc | att | gct | tct | tca | tgt | gga | tta | gtt | tgc | atc | atg | gac | aat | gac | agt | 432 |
| Phe | Ile | Ala | Ser | Ser | Cys | Gly | Leu | Val | Cys | Ile | Met | Asp | Asn | Asp | Ser | |
| | 130 | | | | | 135 | | | | | 140 | | | | | |
| aga | agc | gaa | cta | tat | gtt | tgt | aac | cca | ata | acc | aaa | tgc | agc | aag | aac | 480 |
| Arg | Ser | Glu | Leu | Tyr | Val | Cys | Asn | Pro | Ile | Thr | Lys | Cys | Ser | Lys | Asn | |
| 145 | | | | | 150 | | | | | 155 | | | | | 160 | |
| ctt | cag | gag | cct | cct | ggt | ctc | aag | ttt | tct | gat | tac | agt | gca | ttg | gct | 528 |
| Leu | Gln | Glu | Pro | Pro | Gly | Leu | Lys | Phe | Ser | Asp | Tyr | Ser | Ala | Leu | Ala | |
| | | | | 165 | | | | | 170 | | | | | 175 | | |
| atc | tgt | gca | aac | atg | aaa | act | tct | tgt | tac | agt | gtc | gcc | att | gtt | aaa | 576 |
| Ile | Cys | Ala | Asn | Met | Lys | Thr | Ser | Cys | Tyr | Ser | Val | Ala | Ile | Val | Lys | |
| | | | 180 | | | | | 185 | | | | | 190 | | | |
| tct | aag | caa | gta | cct | ggt | aac | ttc | tat | cag | tgg | gat | ctc | tca | atc | cac | 624 |
| Ser | Lys | Gln | Val | Pro | Gly | Asn | Phe | Tyr | Gln | Trp | Asp | Leu | Ser | Ile | His | |

-continued

```
              195                 200                 205
ata tat gat tct gga aca atg aag tgg ttg acc cct ttg aca gag gtt       672
Ile Tyr Asp Ser Gly Thr Met Lys Trp Leu Thr Pro Leu Thr Glu Val
    210                 215                 220 cta aca ggc tgg aga ggt ggg gat gaa agt gtc atc tgt gat ggt gtt       720
Leu Thr Gly Trp Arg Gly Gly Asp Glu Ser Val Ile Cys Asp Gly Val
225                 230                 235                 240 ttg tac ttc ctg atc tat gca act gga ggt ggt gga cta gaa agt cgt       768
Leu Tyr Phe Leu Ile Tyr Ala Thr Gly Gly Gly Gly Leu Glu Ser Arg
                245                 250                 255 cat ggt ctg atc act tac aac ctc tca agc aga tca tcc cat tgt tcg       816
His Gly Leu Ile Thr Tyr Asn Leu Ser Ser Arg Ser Ser His Cys Ser
            260                 265                 270 tta ata aag act ttc att ccc gtg cca tgt tct cta aca tgt ggt cga       864
Leu Ile Lys Thr Phe Ile Pro Val Pro Cys Ser Leu Thr Cys Gly Arg
        275                 280                 285 ttg atg aac ctc aag gag aag tta gta atg gtg gga ggg att ggg aaa       912
Leu Met Asn Leu Lys Glu Lys Leu Val Met Val Gly Gly Ile Gly Lys
    290                 295                 300 cca gac cgt cct gac ata att aag ggg att ggc ata tgg gca ctt cag       960
Pro Asp Arg Pro Asp Ile Ile Lys Gly Ile Gly Ile Trp Ala Leu Gln
305                 310                 315                 320 ggg aca gaa tgg caa gaa att gcc cgc atg cca cac aag tat ttt caa      1008
Gly Thr Glu Trp Gln Glu Ile Ala Arg Met Pro His Lys Tyr Phe Gln
                325                 330                 335 ggt ttt ggg gaa ttc gat gat gtt ttt gcc agc agt ggc act gat gat      1056
Gly Phe Gly Glu Phe Asp Asp Val Phe Ala Ser Ser Gly Thr Asp Asp
            340                 345                 350 ctc ata tac att cag agt tat gga gct cct gcc ctt ctt gtt ttt gac      1104
Leu Ile Tyr Ile Gln Ser Tyr Gly Ala Pro Ala Leu Leu Val Phe Asp
        355                 360                 365 gtg aac cag aaa cag tgg agg tgg tca cag aaa tgt cca gtg aca aag      1152
Val Asn Gln Lys Gln Trp Arg Trp Ser Gln Lys Cys Pro Val Thr Lys
    370                 375                 380 agg ttt ccc ctt cag ctc ttt act ggt ttc tgc ttc gag caa agg ctt      1200
Arg Phe Pro Leu Gln Leu Phe Thr Gly Phe Cys Phe Glu Gln Arg Leu
385                 390                 395                 400 gag atg tct ccc tga                                                  1215
Glu Met Ser Pro <210> SEQ ID NO 4
<211> LENGTH: 404
<212> TYPE: PRT
<213> ORGANISM: Solanum lycopersicum
<220> FEATURE:
<223> OTHER INFORMATION: Amino acid sequence of mutant cyclin F-box
      protein (from E8986)

<400> SEQUENCE: 4

Met Glu Glu Thr Ser Trp Val Ser His Cys Pro Asp Tyr Val Val Pro
1               5                   10                  15

Asp Met Val Glu Phe Asp Ser Phe Ser Glu Leu Asn Asp Glu Glu Asn
            20                  25                  30

Arg Glu Ala Ser Ser Val Pro Val Asp Leu Ile Leu Pro Asp Asp Leu
        35                  40                  45

Leu Glu Arg Ile Leu Ala Tyr Leu Pro Ile Ala Ser Ile Phe Arg Ala
    50                  55                  60

Ser Cys Val Cys Lys Arg Trp Cys Glu Ile Val Asn Ser Arg Arg Phe
65                  70                  75                  80
```

-continued

```
Leu Trp Asn Phe Ser Gln Val Leu Ser Gln Lys Pro Trp Tyr Phe Met
                 85                  90                  95
Phe Thr Ser Ser Glu Glu Pro Val Gly Tyr Ala Tyr Asp Pro Ser Leu
            100                 105                 110
Arg Lys Trp Tyr Ser Ile Asp Leu Pro Cys Ile Gln Thr Ser Asn Trp
        115                 120                 125
Phe Ile Ala Ser Ser Cys Gly Leu Val Cys Ile Met Asp Asn Asp Ser
130                 135                 140
Arg Ser Glu Leu Tyr Val Cys Asn Pro Ile Thr Lys Cys Ser Lys Asn
145                 150                 155                 160
Leu Gln Glu Pro Pro Gly Leu Lys Phe Ser Asp Tyr Ser Ala Leu Ala
                165                 170                 175
Ile Cys Ala Asn Met Lys Thr Ser Cys Tyr Ser Val Ala Ile Val Lys
            180                 185                 190
Ser Lys Gln Val Pro Gly Asn Phe Tyr Gln Trp Asp Leu Ser Ile His
        195                 200                 205
Ile Tyr Asp Ser Gly Thr Met Lys Trp Leu Thr Pro Leu Thr Glu Val
210                 215                 220
Leu Thr Gly Trp Arg Gly Gly Asp Glu Ser Val Ile Cys Asp Gly Val
225                 230                 235                 240
Leu Tyr Phe Leu Ile Tyr Ala Thr Gly Gly Gly Leu Glu Ser Arg
                245                 250                 255
His Gly Leu Ile Thr Tyr Asn Leu Ser Ser Arg Ser Ser His Cys Ser
            260                 265                 270
Leu Ile Lys Thr Phe Ile Pro Val Pro Cys Ser Leu Thr Cys Gly Arg
        275                 280                 285
Leu Met Asn Leu Lys Glu Lys Leu Val Met Val Gly Gly Ile Gly Lys
290                 295                 300
Pro Asp Arg Pro Asp Ile Ile Lys Gly Ile Gly Ile Trp Ala Leu Gln
305                 310                 315                 320
Gly Thr Glu Trp Gln Glu Ile Ala Arg Met Pro His Lys Tyr Phe Gln
                325                 330                 335
Gly Phe Gly Glu Phe Asp Asp Val Phe Ala Ser Ser Gly Thr Asp Asp
            340                 345                 350
Leu Ile Tyr Ile Gln Ser Tyr Gly Ala Pro Ala Leu Leu Val Phe Asp
        355                 360                 365
Val Asn Gln Lys Gln Trp Arg Trp Ser Gln Lys Cys Pro Val Thr Lys
370                 375                 380
Arg Phe Pro Leu Gln Leu Phe Thr Gly Phe Cys Phe Glu Gln Arg Leu
385                 390                 395                 400
Glu Met Ser Pro
```

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
cccgcatgcc acacaagtat tt                                              22

<210> SEQ ID NO 6
<211> LENGTH: 30
<212> TYPE: DNA
<213> ORGANISM: Artificial

```
<220> FEATURE:
<223> OTHER INFORMATION: primer

<400> SEQUENCE: 6
atcacatatc agggagacat ctcaagccat                                       30

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
ggaaaccaga ccgtcctgac                                                  20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
tgcattgaga ggagctaggg                                                  20

<210> SEQ ID NO 9
<211> LENGTH: 267
<212> TYPE: DNA
<213> ORGANISM: Solanum lycopersicum
<220> FEATURE:
<223> OTHER INFORMATION: analyzed sequence of wild-type Micro-Tom

<400> SEQUENCE: 9
tgggcacttc aggggacaga atggcaagaa attgcccgca tgccacacaa gtattttcaa      60
ggttttgggg aattcgatga tgttttttgcc agcagtggca ctgatgatct catatacatt    120
cagagttatg gagctcctgc ccttcttgtt tttgacgtga accagaaaca gtggaggtgg    180
tcacagaaat gtccagtgac aaagaggttt ccccttcagc tctttactgg tttctgcttc    240
gagccaaggc ttgagatgtc tccctga                                        267

<210> SEQ ID NO 10
<211> LENGTH: 267
<212> TYPE: DNA
<213> ORGANISM: Solanum lycopersicum
<220> FEATURE:
<223> OTHER INFORMATION: analyzed sequence of mutant Micro-Tom (E8986)

<400> SEQUENCE: 10
tgggcacttc aggggacaga atggcaagaa attgcccgca tgccacacaa gtattttcaa      60
ggttttgggg aattcgatga tgttttttgcc agcagtggca ctgatgatct catatacatt    120
cagagttatg gagctcctgc ccttcttgtt tttgacgtga accagaaaca gtggaggtgg    180
tcacagaaat gtccagtgac aaagaggttt ccccttcagc tctttactgg tttctgcttc    240
gagcaaaggc ttgagatgtc tccctga                                        267

<210> SEQ ID NO 11
<211> LENGTH: 20
<212> TYPE: DNA
<213> ORGANISM: Artificial
<220> FEATURE:
<223> OTHER INFORMATION: primer
```

```
<400> SEQUENCE: 11
ccacagcctt agggttggag                                                    20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
acggtctggt ttcccaatcc                                                    20

<210> SEQ ID NO 13
<211> LENGTH: 22
<212> TYPE: DNA
<213> ORGANISM: Artificial
<220> FEATURE:
<223> OTHER INFORMATION: primer

<400> SEQUENCE: 13
gcattggcta tctgtgcaaa ca                                                 22

<210> SEQ ID NO 14
<211> LENGTH: 22
<212> TYPE: DNA
<213> ORGANISM: Artificial
<220> FEATURE:
<223> OTHER INFORMATION: primer

<400> SEQUENCE: 14
agacaacttg tccctgtctt gg                                                 22

<210> SEQ ID NO 15
<211> LENGTH: 22
<212> TYPE: DNA
<213> ORGANISM: Artificial
<220> FEATURE:
<223> OTHER INFORMATION: primer

<400> SEQUENCE: 15
ttctggaaca atgaagtggt tg                                                 22

<210> SEQ ID NO 16
<211> LENGTH: 36
<212> TYPE: DNA
<213> ORGANISM: Artificial
<220> FEATURE:
<223> OTHER INFORMATION: primer

<400> SEQUENCE: 16
ccttaattat gtcaggacgg tctggtttca caatcc                                  36

<210> SEQ ID NO 17
<211> LENGTH: 44
<212> TYPE: DNA
<213> ORGANISM: Artificial
<220> FEATURE:
<223> OTHER INFORMATION: primer

<400> SEQUENCE: 17
ttcattttca gagcttaatg atgaagaaaa tagagaggct tccc                         44

<210> SEQ ID NO 18
<211> LENGTH: 23
```

```
<212> TYPE: DNA
<213> ORGANISM: Artificial
<220> FEATURE:
<223> OTHER INFORMATION: primer

<400> SEQUENCE: 18
tgaatgcaag ggaggtcaat act                                          23

<210> SEQ ID NO 19
<211> LENGTH: 1215
<212> TYPE: DNA
<213> ORGANISM: Solanum lycopersicum
<220> FEATURE:
<221> NAME/KEY: CDS
<222> LOCATION: (1)..(1215)
<220> FEATURE:
<223> OTHER INFORMATION: CDS sequence encoding wild-type cyclin F-box
      protein (from W3583)

<400> SEQUENCE: 19
```

| | | | | | | | | | | | | | | | | |
|---|---|---|---|---|---|---|---|---|---|---|---|---|---|---|---|---|
| atg | gaa | gaa | acc | tct | tgg | gtc | agt | cat | tgc | cct | gat | tac | gtt | gta | cca | 48 |
| Met | Glu | Glu | Thr | Ser | Trp | Val | Ser | His | Cys | Pro | Asp | Tyr | Val | Val | Pro | |
| 1 | | | | 5 | | | | | 10 | | | | | 15 | | |
| gac | atg | gtt | gag | ttt | gat | tca | ttt | tca | gag | ctt | aat | gat | gaa | gaa | aat | 96 |
| Asp | Met | Val | Glu | Phe | Asp | Ser | Phe | Ser | Glu | Leu | Asn | Asp | Glu | Glu | Asn | |
| | | | 20 | | | | | 25 | | | | | 30 | | | |
| aga | gag | gct | tcc | tta | gtt | cct | gtg | gat | ttg | ata | ctg | cct | gat | gat | tta | 144 |
| Arg | Glu | Ala | Ser | Leu | Val | Pro | Val | Asp | Leu | Ile | Leu | Pro | Asp | Asp | Leu | |
| | | 35 | | | | | 40 | | | | | 45 | | | | |
| ctg | gaa | cgc | ata | ctg | gcc | tat | ctt | ccc | att | gcc | agc | att | ttt | agg | gca | 192 |
| Leu | Glu | Arg | Ile | Leu | Ala | Tyr | Leu | Pro | Ile | Ala | Ser | Ile | Phe | Arg | Ala | |
| 50 | | | | | 55 | | | | | 60 | | | | | | |
| agt | tgt | gtg | tgt | aaa | aga | tgg | tgt | gag | ata | gtg | aat | tca | aga | agg | ttt | 240 |
| Ser | Cys | Val | Cys | Lys | Arg | Trp | Cys | Glu | Ile | Val | Asn | Ser | Arg | Arg | Phe | |
| 65 | | | | | 70 | | | | | 75 | | | | | 80 | |
| tta | tgg | aac | ttc | tct | cag | gtg | ctg | tct | caa | aaa | ccg | tgg | tac | ttt | atg | 288 |
| Leu | Trp | Asn | Phe | Ser | Gln | Val | Leu | Ser | Gln | Lys | Pro | Trp | Tyr | Phe | Met | |
| | | | | 85 | | | | | 90 | | | | | 95 | | |
| ttc | aca | agc | tca | gag | gag | cca | gtt | ggt | tat | gcc | tat | gat | cct | tcc | ctt | 336 |
| Phe | Thr | Ser | Ser | Glu | Glu | Pro | Val | Gly | Tyr | Ala | Tyr | Asp | Pro | Ser | Leu | |
| | | | 100 | | | | | 105 | | | | | 110 | | | |
| cga | aaa | tgg | tat | agt | att | gac | ctc | cct | tgc | att | cag | aca | tca | aat | tgg | 384 |
| Arg | Lys | Trp | Tyr | Ser | Ile | Asp | Leu | Pro | Cys | Ile | Gln | Thr | Ser | Asn | Trp | |
| | | 115 | | | | | 120 | | | | | 125 | | | | |
| ttc | att | gct | tct | tca | tgt | gga | tta | gtt | tgc | atc | atg | gac | aat | gac | agt | 432 |
| Phe | Ile | Ala | Ser | Ser | Cys | Gly | Leu | Val | Cys | Ile | Met | Asp | Asn | Asp | Ser | |
| 130 | | | | | 135 | | | | | 140 | | | | | | |
| aga | agc | gaa | cta | tat | gtt | tgt | aac | cca | ata | acc | aaa | tgc | agc | aag | aac | 480 |
| Arg | Ser | Glu | Leu | Tyr | Val | Cys | Asn | Pro | Ile | Thr | Lys | Cys | Ser | Lys | Asn | |
| 145 | | | | | 150 | | | | | 155 | | | | | 160 | |
| ctt | cag | gag | cct | cct | ggt | ctc | aag | ttt | tct | gat | tac | agt | gca | ttg | gct | 528 |
| Leu | Gln | Glu | Pro | Pro | Gly | Leu | Lys | Phe | Ser | Asp | Tyr | Ser | Ala | Leu | Ala | |
| | | | | 165 | | | | | 170 | | | | | 175 | | |
| atc | tgt | gca | aac | atg | aaa | act | tct | tgt | tac | agt | gtc | gcc | att | gtt | aaa | 576 |
| Ile | Cys | Ala | Asn | Met | Lys | Thr | Ser | Cys | Tyr | Ser | Val | Ala | Ile | Val | Lys | |
| | | | 180 | | | | | 185 | | | | | 190 | | | |
| tct | aag | caa | gta | cct | gga | aac | ttc | tat | cag | tgg | gat | ctc | tca | atc | cac | 624 |
| Ser | Lys | Gln | Val | Pro | Gly | Asn | Phe | Tyr | Gln | Trp | Asp | Leu | Ser | Ile | His | |
| | | 195 | | | | | 200 | | | | | 205 | | | | |
| ata | tat | gat | tct | gga | aca | atg | aag | tgg | ttg | acc | cct | ttg | aca | gag | gtt | 672 |
| Ile | Tyr | Asp | Ser | Gly | Thr | Met | Lys | Trp | Leu | Thr | Pro | Leu | Thr | Glu | Val | |
| 210 | | | | | 215 | | | | | 220 | | | | | | |

```
cta aca ggc tgg aga ggt ggg gat gaa agt gtc atc tgt gat ggt gtt      720
Leu Thr Gly Trp Arg Gly Gly Asp Glu Ser Val Ile Cys Asp Gly Val
225             230                 235                 240 ttg tac ttc ctg atc tat gca act gga ggt ggt gga cta gaa agt cgt      768
Leu Tyr Phe Leu Ile Tyr Ala Thr Gly Gly Gly Gly Leu Glu Ser Arg
            245                 250                 255 cat ggt ctg atc act tac aac ctc tca agc aga tca tcc cat tgt tcg      816
His Gly Leu Ile Thr Tyr Asn Leu Ser Ser Arg Ser Ser His Cys Ser
        260                 265                 270 tta ata aag act ttc att ccc gtg cca tgt tct cta aca tgt ggt cga      864
Leu Ile Lys Thr Phe Ile Pro Val Pro Cys Ser Leu Thr Cys Gly Arg
    275                 280                 285 ttg atg aac ctc aag gag aag tta gta atg gtg gga ggg att ggg aaa      912
Leu Met Asn Leu Lys Glu Lys Leu Val Met Val Gly Gly Ile Gly Lys
290                 295                 300 cca gac cgt cct gac ata att aag ggg att ggc ata tgg gca ctt cag      960
Pro Asp Arg Pro Asp Ile Ile Lys Gly Ile Gly Ile Trp Ala Leu Gln
305             310                 315                 320 ggg aca gaa tgg caa gaa att gcc cgc atg cca cac aag tat ttt caa     1008
Gly Thr Glu Trp Gln Glu Ile Ala Arg Met Pro His Lys Tyr Phe Gln
            325                 330                 335 ggt ttt ggg gaa ttc gat gat gtt ttt gcc agc agt ggc act gat gat     1056
Gly Phe Gly Glu Phe Asp Asp Val Phe Ala Ser Ser Gly Thr Asp Asp
        340                 345                 350 ctc ata tac att cag agt tat gga gct cct gcc ctt ctt gtt ttt gac     1104
Leu Ile Tyr Ile Gln Ser Tyr Gly Ala Pro Ala Leu Leu Val Phe Asp
    355                 360                 365 gtg aac cag aaa cag tgg agg tgg tca cag aaa tgt cca gtg aca aag     1152
Val Asn Gln Lys Gln Trp Arg Trp Ser Gln Lys Cys Pro Val Thr Lys
370                 375                 380 agg ttt ccc ctt cag ctc ttt act ggt ttc tgc ttc gag cca agg ctt     1200
Arg Phe Pro Leu Gln Leu Phe Thr Gly Phe Cys Phe Glu Pro Arg Leu
385             390                 395                 400 gag atg tct ccc tga                                                 1215
Glu Met Ser Pro <210> SEQ ID NO 20
<211> LENGTH: 404
<212> TYPE: PRT
<213> ORGANISM: Solanum lycopersicum
<220> FEATURE:
<223> OTHER INFORMATION: Amino acid sequence of wild-type cyclin F-box
      protein

<400> SEQUENCE: 20

Met Glu Glu Thr Ser Trp Val Ser His Cys Pro Asp Tyr Val Val Pro
1               5                   10                  15

Asp Met Val Glu Phe Asp Ser Phe Ser Glu Leu Asn Asp Glu Glu Asn
            20                  25                  30

Arg Glu Ala Ser Leu Val Pro Val Asp Leu Ile Leu Pro Asp Asp Leu
        35                  40                  45

Leu Glu Arg Ile Leu Ala Tyr Leu Pro Ile Ala Ser Ile Phe Arg Ala
    50                  55                  60

Ser Cys Val Cys Lys Arg Trp Cys Glu Ile Val Asn Ser Arg Arg Phe
65                  70                  75                  80

Leu Trp Asn Phe Ser Gln Val Leu Ser Gln Lys Pro Trp Tyr Phe Met
                85                  90                  95

Phe Thr Ser Ser Glu Glu Pro Val Gly Tyr Ala Tyr Asp Pro Ser Leu
            100                 105                 110
```

```
Arg Lys Trp Tyr Ser Ile Asp Leu Pro Cys Ile Gln Thr Ser Asn Trp
            115                 120                 125

Phe Ile Ala Ser Ser Cys Gly Leu Val Cys Ile Met Asp Asn Asp Ser
    130                 135                 140

Arg Ser Glu Leu Tyr Val Cys Asn Pro Ile Thr Lys Cys Ser Lys Asn
145                 150                 155                 160

Leu Gln Glu Pro Pro Gly Leu Lys Phe Ser Asp Tyr Ser Ala Leu Ala
                165                 170                 175

Ile Cys Ala Asn Met Lys Thr Ser Cys Tyr Ser Val Ala Ile Val Lys
            180                 185                 190

Ser Lys Gln Val Pro Gly Asn Phe Tyr Gln Trp Asp Leu Ser Ile His
        195                 200                 205

Ile Tyr Asp Ser Gly Thr Met Lys Trp Leu Thr Pro Leu Thr Glu Val
    210                 215                 220

Leu Thr Gly Trp Arg Gly Gly Asp Glu Ser Val Ile Cys Asp Gly Val
225                 230                 235                 240

Leu Tyr Phe Leu Ile Tyr Ala Thr Gly Gly Gly Leu Glu Ser Arg
                245                 250                 255

His Gly Leu Ile Thr Tyr Asn Leu Ser Ser Arg Ser Ser His Cys Ser
            260                 265                 270

Leu Ile Lys Thr Phe Ile Pro Val Pro Cys Ser Leu Thr Cys Gly Arg
        275                 280                 285

Leu Met Asn Leu Lys Glu Lys Leu Val Met Val Gly Gly Ile Gly Lys
    290                 295                 300

Pro Asp Arg Pro Asp Ile Ile Lys Gly Ile Gly Ile Trp Ala Leu Gln
305                 310                 315                 320

Gly Thr Glu Trp Gln Glu Ile Ala Arg Met Pro His Lys Tyr Phe Gln
                325                 330                 335

Gly Phe Gly Glu Phe Asp Asp Val Phe Ala Ser Ser Gly Thr Asp Asp
            340                 345                 350

Leu Ile Tyr Ile Gln Ser Tyr Gly Ala Pro Ala Leu Leu Val Phe Asp
        355                 360                 365

Val Asn Gln Lys Gln Trp Arg Trp Ser Gln Lys Cys Pro Val Thr Lys
370                 375                 380

Arg Phe Pro Leu Gln Leu Phe Thr Gly Phe Cys Phe Glu Pro Arg Leu
385                 390                 395                 400

Glu Met Ser Pro

<210> SEQ ID NO 21
<211> LENGTH: 1215
<212> TYPE: DNA
<213> ORGANISM: Solanum lycopersicum
<220> FEATURE:
<221> NAME/KEY: CDS
<222> LOCATION: (1)..(1215)
<220> FEATURE:
<223> OTHER INFORMATION: CDS sequence encoding wild-type cyclin F-box
      protein (from W283)

<400> SEQUENCE: 21 atg gaa gaa acc tct tgg gtc agt cat tgc cct gat tac gtt gta cca      48
Met Glu Glu Thr Ser Trp Val Ser His Cys Pro Asp Tyr Val Val Pro
1               5                   10                  15 gac atg gtt gag ttt gat tca ttt tca gag ctt aat gat gaa gaa aat      96
Asp Met Val Glu Phe Asp Ser Phe Ser Glu Leu Asn Asp Glu Glu Asn
                20                  25                  30 aga gag gct tcc tca gtt cct gtg gat ttg ata ctg cct gat gat tta    144
```

```
               Arg Glu Ala Ser Ser Val Pro Val Asp Leu Ile Leu Pro Asp Asp Leu
                       35                  40                  45 ctg gaa cgc ata ctg gcc tat ctt ccc att gcc agc att ttt agg gca       192
Leu Glu Arg Ile Leu Ala Tyr Leu Pro Ile Ala Ser Ile Phe Arg Ala
    50                  55                  60 agt tgt gtg tgt aaa aga tgg tgt gag ata gtg aat tca aga agg ttt       240
Ser Cys Val Cys Lys Arg Trp Cys Glu Ile Val Asn Ser Arg Arg Phe
65                  70                  75                  80 tta tgg aac ttc tct cag gtg ctg tct caa aaa ccg tgg tac ttt atg       288
Leu Trp Asn Phe Ser Gln Val Leu Ser Gln Lys Pro Trp Tyr Phe Met
                85                  90                  95 ttc aca agc tca gag gag cca gtt ggt tat gcc tat gat cct tcc ctt       336
Phe Thr Ser Ser Glu Glu Pro Val Gly Tyr Ala Tyr Asp Pro Ser Leu
            100                 105                 110 cga aaa tgg tat agt att gac ctc cct tgc att cag aca tca aat tgg       384
Arg Lys Trp Tyr Ser Ile Asp Leu Pro Cys Ile Gln Thr Ser Asn Trp
        115                 120                 125 ttc att gct tct tca tgt gga tta gtt tgc atc atg gac aat gac agt       432
Phe Ile Ala Ser Ser Cys Gly Leu Val Cys Ile Met Asp Asn Asp Ser
    130                 135                 140 aga agc gaa cta tat gtt tgt aac cca ata acc aaa tgc agc aag aac       480
Arg Ser Glu Leu Tyr Val Cys Asn Pro Ile Thr Lys Cys Ser Lys Asn
145                 150                 155                 160 ctt cag gag cct cct ggt ctc aag ttt tct gat tac agt gca ttg gct       528
Leu Gln Glu Pro Pro Gly Leu Lys Phe Ser Asp Tyr Ser Ala Leu Ala
                165                 170                 175 atc tgt gca aac atg aaa act tct tgt tac agt gtc gcc att gtt aaa       576
Ile Cys Ala Asn Met Lys Thr Ser Cys Tyr Ser Val Ala Ile Val Lys
            180                 185                 190 tct aag caa gta cct ggt aac ttc tat cag tgg gat ctc tca atc cac       624
Ser Lys Gln Val Pro Gly Asn Phe Tyr Gln Trp Asp Leu Ser Ile His
        195                 200                 205 ata tat gat tct gga aca atg aag tgg ttg acc cct ttg aca gag gtt       672
Ile Tyr Asp Ser Gly Thr Met Lys Trp Leu Thr Pro Leu Thr Glu Val
    210                 215                 220 cta aca ggc tgg aga ggt ggg gat gaa agt gtc atc tgt gat ggt gtt       720
Leu Thr Gly Trp Arg Gly Gly Asp Glu Ser Val Ile Cys Asp Gly Val
225                 230                 235                 240 ttg tac ttc ctg atc tat gca act gga ggt ggt gga cta gaa agt cgt       768
Leu Tyr Phe Leu Ile Tyr Ala Thr Gly Gly Gly Gly Leu Glu Ser Arg
                245                 250                 255 cat ggt ctg atc act tac aac ctc tca agc aga tca tcc cat tgt tcg       816
His Gly Leu Ile Thr Tyr Asn Leu Ser Ser Arg Ser Ser His Cys Ser
            260                 265                 270 tta ata aag act ttc att ccc gtg cca tgt tct cta aca tgt ggt cga       864
Leu Ile Lys Thr Phe Ile Pro Val Pro Cys Ser Leu Thr Cys Gly Arg
        275                 280                 285 ttg atg aac ctc aag gag aag tta gta atg gtg gga agg att ggg aaa       912
Leu Met Asn Leu Lys Glu Lys Leu Val Met Val Gly Arg Ile Gly Lys
    290                 295                 300 cca gac cgt cct gac ata att aag ggg att ggc ata tgg gca ctt cag       960
Pro Asp Arg Pro Asp Ile Ile Lys Gly Ile Gly Ile Trp Ala Leu Gln
305                 310                 315                 320 ggg aca gaa tgg caa gaa att gcc cgc atg cca cac aag tat ttt caa      1008
Gly Thr Glu Trp Gln Glu Ile Ala Arg Met Pro His Lys Tyr Phe Gln
                325                 330                 335 ggt ttt ggg gaa ttc gat gat gtt ttt gcc agc agt ggc act gat gat      1056
Gly Phe Gly Glu Phe Asp Asp Val Phe Ala Ser Ser Gly Thr Asp Asp
            340                 345                 350
```

-continued

```
ctc ata tac att cag agt tat gga gct cct gcc ctt ctt gtt ttt gac    1104
Leu Ile Tyr Ile Gln Ser Tyr Gly Ala Pro Ala Leu Leu Val Phe Asp
        355                 360                 365 gtg aac cag aaa cag tgg agg tgg tca cag aaa tgt cca gtg aca aag    1152
Val Asn Gln Lys Gln Trp Arg Trp Ser Gln Lys Cys Pro Val Thr Lys
370                 375                 380 agg ttt ccc ctt cag ctc ttt act ggt ttc tgc ttc gag cca agg ctt    1200
Arg Phe Pro Leu Gln Leu Phe Thr Gly Phe Cys Phe Glu Pro Arg Leu
385                 390                 395                 400 gag atg tct ccc tga                                                1215
Glu Met Ser Pro
```

<210> SEQ ID NO 22
<211> LENGTH: 404
<212> TYPE: PRT
<213> ORGANISM: Solanum lycopersicum
<220> FEATURE:
<223> OTHER INFORMATION: Amino acid sequence of wild-type cyclin F-box
      protein (from W283)

<400> SEQUENCE: 22

```
Met Glu Glu Thr Ser Trp Val Ser His Cys Pro Asp Tyr Val Val Pro
1               5                   10                  15

Asp Met Val Glu Phe Asp Ser Phe Ser Glu Leu Asn Asp Glu Asn
            20                  25                  30

Arg Glu Ala Ser Ser Val Pro Val Asp Leu Ile Leu Pro Asp Asp Leu
        35                  40                  45

Leu Glu Arg Ile Leu Ala Tyr Leu Pro Ile Ala Ser Ile Phe Arg Ala
    50                  55                  60

Ser Cys Val Cys Lys Arg Trp Cys Glu Ile Val Asn Ser Arg Arg Phe
65                  70                  75                  80

Leu Trp Asn Phe Ser Gln Val Leu Ser Gln Lys Pro Trp Tyr Phe Met
                85                  90                  95

Phe Thr Ser Ser Glu Glu Pro Val Gly Tyr Ala Tyr Asp Pro Ser Leu
            100                 105                 110

Arg Lys Trp Tyr Ser Ile Asp Leu Pro Cys Ile Gln Thr Ser Asn Trp
        115                 120                 125

Phe Ile Ala Ser Ser Cys Gly Leu Val Cys Ile Met Asp Asn Asp Ser
    130                 135                 140

Arg Ser Glu Leu Tyr Val Cys Asn Pro Ile Thr Lys Cys Ser Lys Asn
145                 150                 155                 160

Leu Gln Glu Pro Pro Gly Leu Lys Phe Ser Asp Tyr Ser Ala Leu Ala
                165                 170                 175

Ile Cys Ala Asn Met Lys Thr Ser Cys Tyr Ser Val Ala Ile Val Lys
            180                 185                 190

Ser Lys Gln Val Pro Gly Asn Phe Tyr Gln Trp Asp Leu Ser Ile His
        195                 200                 205

Ile Tyr Asp Ser Gly Thr Met Lys Trp Leu Thr Pro Leu Thr Glu Val
    210                 215                 220

Leu Thr Gly Trp Arg Gly Gly Asp Glu Ser Val Ile Cys Asp Gly Val
225                 230                 235                 240

Leu Tyr Phe Leu Ile Tyr Ala Thr Gly Gly Gly Leu Glu Ser Arg
                245                 250                 255

His Gly Leu Ile Thr Tyr Asn Leu Ser Ser Arg Ser Ser His Cys Ser
            260                 265                 270

Leu Ile Lys Thr Phe Ile Pro Val Pro Cys Ser Leu Thr Cys Gly Arg
        275                 280                 285
```

```
Leu Met Asn Leu Lys Glu Lys Leu Val Met Val Gly Arg Ile Gly Lys
    290                 295                 300

Pro Asp Arg Pro Asp Ile Ile Lys Gly Ile Gly Ile Trp Ala Leu Gln
305                 310                 315                 320

Gly Thr Glu Trp Gln Glu Ile Ala Arg Met Pro His Lys Tyr Phe Gln
                325                 330                 335

Gly Phe Gly Glu Phe Asp Asp Val Phe Ala Ser Ser Gly Thr Asp Asp
                340                 345                 350

Leu Ile Tyr Ile Gln Ser Tyr Gly Ala Pro Ala Leu Leu Val Phe Asp
                355                 360                 365

Val Asn Gln Lys Gln Trp Arg Trp Ser Gln Lys Cys Pro Val Thr Lys
    370                 375                 380

Arg Phe Pro Leu Gln Leu Phe Thr Gly Phe Cys Phe Glu Pro Arg Leu
385                 390                 395                 400

Glu Met Ser Pro

<210> SEQ ID NO 23
<211> LENGTH: 36
<212> TYPE: DNA
<213> ORGANISM: Solanum lycopersicum

<400> SEQUENCE: 23
ggtttctgct tcgagccaag gcttgagatg tctccc                                36

<210> SEQ ID NO 24
<211> LENGTH: 12
<212> TYPE: PRT
<213> ORGANISM: Solanum lycopersicum

<400> SEQUENCE: 24

Gly Phe Cys Phe Glu Pro Arg Leu Glu Met Ser Pro
1               5                   10

<210> SEQ ID NO 25
<211> LENGTH: 36
<212> TYPE: DNA
<213> ORGANISM: Solanum lycopersicum

<400> SEQUENCE: 25
ggtttctgct tcgagcaaag gcttgagatg tctccc                                36

<210> SEQ ID NO 26
<211> LENGTH: 12
<212> TYPE: PRT
<213> ORGANISM: Solanum lycopersicum

<400> SEQUENCE: 26

Gly Phe Cys Phe Glu Gln Arg Leu Glu Met Ser Pro
1               5                   10
```

PLANT HAVING MUTANT CYCLIN F-BOX GENE

This application is a 371 application of PCT/JP2016/073164 having an international filing date of Aug. 5, 2016, which claims priority to JP2015-156140 filed Aug. 6, 2015, the entire content of each of which is incorporated herein by reference.

TECHNICAL FIELD

The present invention relates to a plant having a mutant cyclin F-box gene, and especially a plant having a mutant cyclin F-box gene that confers parthenocarpy and/or a high sugar content in fruit.

BACKGROUND ART

In recent years, there is an increasing demand for tomatoes and especially high-sugar content tomatoes have been becoming popular. In order to achieve high sugar contents of tomatoes, a load of water stress (restriction of the amount of water supplied to or absorbed by tomato plants) during cultivation is widely employed. There are various known cultivation methods, equipment, and the like for achieving high sugar contents of tomatoes by the load of water stress (e.g., Patent Literature 1 to 2). Treatment with an agent for improving sugar contents (Patent Literature 3 to 5), red light irradiation treatment after the end of the light period (Patent Literature 6), and the like are also known as techniques for achieving high sugar contents of tomatoes. However, conventional techniques for achieving high sugar contents require specialized cultivation technology and cultivation facilities, and therefore, there are still many problems in terms of economic efficiency, labor efficiency, and stability. Development of a new technology for achieving high sugar contents of tomatoes with decreased labor and cost has been awaited.

Meanwhile, although tomatoes are self-pollinating plants, it is known that the greenhouse cultivation of tomato results in reduced pollination and fruit-setting rates due to lack of wind and insects which assist pollination. Therefore, methods for promoting parthenocarpy and fruit enlargement by plant hormone treatment of flower trusses are widely used. Alternatively, methods for promoting pollination using bumblebees or vibrators are also widely used. However, plant hormone treatment and treatment for promoting pollination using vibrators require a lot of labor, which results in a significant decrease in labor efficiency. Although labor efficiency of a method using bumblebees is good, the method is problematic in causing an increase in cost and effort for temperature control in a facility in the summer and winter, due to the limitation of the temperature range for activity of bumblebees. In addition, reduction of pollen fertility in summer and winter makes it difficult to secure stable fruit production throughout a year in the case of fruit-setting via pollination/fertilization, which is also problematic. Therefore, to realize stable cultivation with decreased labor and cost while reducing influence of environmental factors such as seasonal factors, there is a demand for development of technology for inducing parthenocarpy in tomato plants at improved work efficiency.

Relatively new techniques for inducing parthenocarpy of tomato plants include a method using a non-plant hormonal fruit-setting promoter (e.g., Patent Literature 7) and a method for introducing a parthenocarpic gene into tomato plants (Patent Literature 8 to 9). However, the method using a fruit-setting promoter is still problematic in terms of labor efficiency. In addition, a parthenocarpic tomato variety that is produced using a conventional parthenocarpic gene is problematic in terms of fruit quality due to softening or the like. In view of the above, development of a tomato variety having parthenocarpy and preferable fruit characteristics has been awaited.

Further, development of a parthenocarpic induction method that allows stable fruit production with labor-saving and low-cost has been awaited not only for tomato plants but also for many of other cultivation plants.

CITATION LIST

Patent Literature

Patent Literature 1: JP Patent Publication No. 2012-100595 A
Patent Literature 2: JP Patent Publication No. 2012-161289 A
Patent Literature 3: International Publication WO 2005/094557
Patent Literature 4: International Publication WO 2009/063806
Patent Literature 5: International Publication WO 2010/021330
Patent Literature 6: JP Patent Publication No. 2012-65601 A
Patent Literature 7: JP Patent Publication No. 2004-331507 A
Patent Literature 8: International Publication WO 99/21411
Patent Literature 9: International Publication WO 2009/005343

SUMMARY OF INVENTION

Technical Problem

It is an object of the present invention to provide a plant having an improved sugar content in fruit and a method for producing thereof. It is another object of the present invention to provide a parthenocarpic plant and a method for producing thereof.

Solution to Problem

As a result of intensive studies to solve the above-described problems, the present inventors found that a gene function-altering mutation in the cyclin F-box gene confers parthenocarpy and increases the sugar content in fruit in plants such as tomatoes. This has led to the completion of the present invention.

Specifically, the present invention encompasses the following.

[1] A parthenocarpic plant having a mutant cyclin F-box gene comprising a nucleotide mutation that causes a non-conservative amino acid substitution of proline at position 398 defined based on the amino acid sequence set forth in SEQ ID NO: 2 in a cyclin F-box protein.

[2] The plant according to [1], wherein the plant has an improved sugar content in fruit.

[3] The plant according to [1] or [2], wherein the plant is tomato.

[4] The plant according to any one of [1] to [3], wherein the non-conservative amino acid substitution of proline is a substitution of proline by glutamine.

[5] The plant according to any one of [1] to [4], wherein the plant is a seed or fruit.

[6] A method for producing a parthenocarpic plant, comprising introducing a nucleotide mutation that causes a non-conservative amino acid substitution of proline at position 398 defined based on the amino acid sequence set forth in SEQ ID NO: 2 in a cyclin F-box protein into a cyclin F-box gene of a plant.

[7] A method for producing a plant having an improved sugar content in fruit, comprising introducing a nucleotide mutation that causes a non-conservative amino acid substitution of proline at position 398 defined based on the amino acid sequence set forth in SEQ ID NO: 2 in a cyclin F-box protein into the cyclin F-box gene of a plant.

[8] The method according to [6] or [7], wherein the non-conservative amino acid substitution of proline is a substitution of proline by glutamine.

[9] The method according to any one of [6] to [8], wherein the plant is tomato.

[10] A method of plant breeding, comprising crossing plants using the plant according to any one of [1] to [4] as a breeding parent, obtaining progeny plants and selecting a progeny plant having said mutant cyclin F-box gene introduced thereinto.

[11] The method according to [10], wherein the progeny plant is selected by detecting the mutant cyclin F-box gene in the progeny plant.

[12] A primer set, comprising a primer comprising the nucleotide sequence set forth in SEQ ID NO: 5 and a primer comprising the nucleotide sequence set forth in SEQ ID NO: 6.

[13] A kit for use in tomato plant breeding, comprising the primer set according to [12].

[14] A mutant cyclin F-box gene, which encodes:
  (i) the amino acid sequence set forth in SEQ ID NO: 4, or
  (ii) an amino acid sequence that has 80% or more sequence identity to the amino acid sequence set forth in SEQ ID NO: 2 and comprises a substitution of proline at position 398 defined based on the amino acid sequence set forth in SEQ ID NO: 2 by glutamine;
  and confers parthenocarpy.

[15] A plant having an improved sugar content in fruit compared with wild type, wherein the plant has a mutant cyclin F-box gene comprising a nucleotide mutation that causes a non-conservative amino acid substitution of serine at position 37 or glycine at position 301 defined based on the amino acid sequence set forth in SEQ ID NO: 2 in a cyclin F-box protein.

[16] The plant according to [15], wherein the plant is tomato.

[17] The plant according to [15] or [16], wherein the non-conservative amino acid substitution of serine at position 37 is a substitution of serine by leucine.

[18] The plant according to [15] or [16], wherein the non-conservative amino acid substitution of glycine at position 301 is a substitution of glycine by arginine.

[19] The plant according to any one of [15] to [18], which is a seed or fruit.

[20] A method for producing a plant having an improved sugar content in fruit, comprising introducing a nucleotide mutation that causes a non-conservative amino acid substitution of serine at position 37 or glycine at position 301 defined based on the amino acid sequence set forth in SEQ ID NO: 2 in a cyclin F-box protein, into a cyclin F-box gene of a plant.

[21] The method according to claim 20, wherein the plant is tomato.

[22] The method according to claim 20 or 21, wherein the non-conservative amino acid substitution of serine at position 37 is a substitution of serine by leucine.

[23] The method according to claim 20 or 21, wherein the non-conservative amino acid substitution of glycine at position 301 is a substitution of glycine by arginine.

[24] A method of plant breeding, comprising crossing plants using the plant according to any one of claims 15 to 18 as a breeding parent, obtaining progeny plants and selecting a progeny plant having said mutant cyclin F-box gene introduced thereinto.

[25] The method according to claim 24, wherein the progeny plant is selected by detecting the mutant cyclin F-box gene in the progeny plant.

[26] A primer set, comprising a primer comprising the nucleotide sequence set forth in SEQ ID NO: 15 and a primer comprising the nucleotide sequence set forth in SEQ ID NO: 16.

[27] A primer set, comprising a primer comprising the nucleotide sequence set forth in SEQ ID NO: 17 and a primer comprising the nucleotide sequence set forth in SEQ ID NO: 18.

[28] A kit for use in tomato plant breeding, comprising the primer set according to claim 26 or 27.

[29] A mutant cyclin F-box gene, which encodes:
  (i) the amino acid sequence set forth in SEQ ID NO: 20 or 22, or
  (ii) an amino acid sequence that has 80% or more sequence identity to the amino acid sequence set forth in SEQ ID NO: 2 and comprises a substitution of serine at position 37 by leucine or a substitution of glycine at position 301 by arginine, as defined based on the amino acid sequence set forth in SEQ ID NO: 2;
  and confers an improved sugar content in fruit.

[30] A method for screening for a plant having an improved sugar content in fruit, comprising introducing a nucleotide mutation that causes a non-conservative amino acid substitution into a cyclin F-box gene of a plant and selecting a plant having an improved sugar content in fruit compared with wild type plant.

The present description includes the disclosures in Japanese Patent Application No. 2015-156140, to which the present application claims a priority.

Advantageous Effects of Invention

The present invention facilitates production of a plant having parthenocarpy and/or an improved sugar content in fruit.

DESCRIPTION OF EMBODIMENTS

Figure 1:
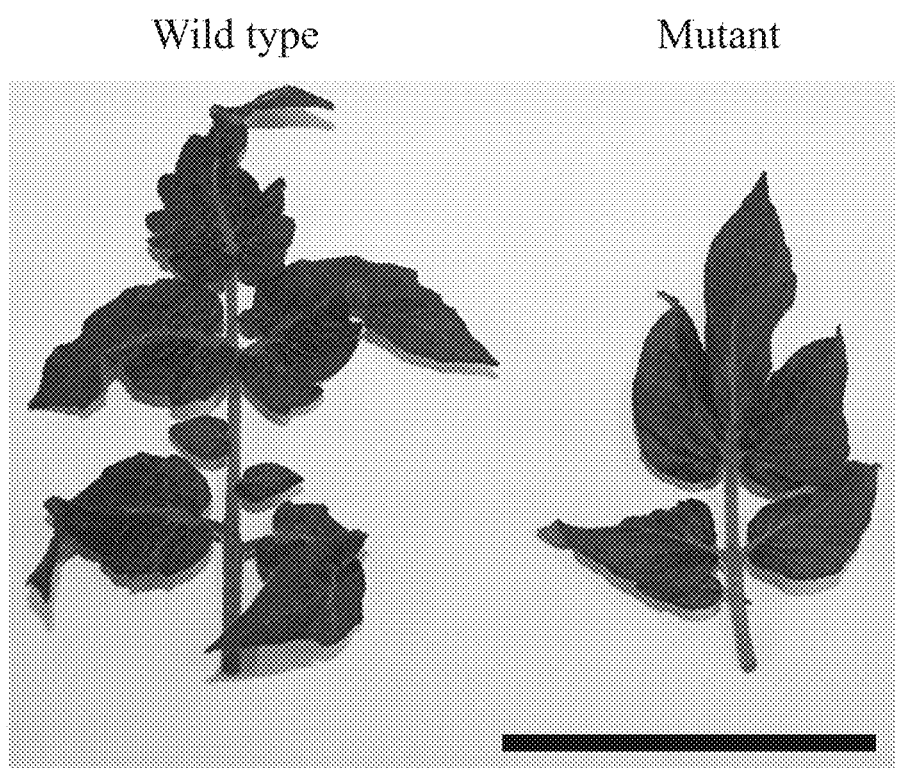
FIG. 1 is a photograph showing morphology of leaves of wild type and mutant tomato plants. Bar=5 cm.

Hereinafter, the present invention will be described in detail.

The present invention relates to a plant having a gene encoding a mutant cyclin F-box protein, which has a nucleotide mutation that causes a non-conservative amino acid substitution and confers parthenocarpy and/or a high sugar content in fruit; and a method for producing thereof. In one embodiment, the present invention relates to a plant having a mutant cyclin F-box gene that contains a gene function-altering mutation that confers parthenocarpy; and a method for producing thereof. In the context of the present invention, the "mutant" cyclin F-box gene refers to a gene containing a nucleotide mutation that causes alterations in the gene function in the nucleotide sequence of the wild type cyclin F-box gene. The plant according to the present invention has the mutant cyclin F-box gene that contains a gene function-altering mutation providing parthenocarpy, which allows the plant to acquire parthenocarpic ability. In addition, the plant of the present invention preferably has an improved sugar content in fruit compared with a plant having the wild type cyclin F-box gene due to the mutant cyclin F-box gene. The improvement of sugar content in fruit is shown even in pollinated fruits and particularly significantly shown in parthenocarpic fruits.

In the context of the present invention, the term "parthenocarpy" refers to production of seedless fruits without pollination and fertilization in a plant, exhibiting enlargement of ovary, receptacles or the like without seed formation. In the context of the present invention, the terms "parthenocarpic" and "parthenocarpic ability" refer to the property and the ability of a plant to cause parthenocarpy without the need for artificial parthenocarpic induction treatment such as plant hormone treatment or a certain physical stimulation, respectively.

Plants used in the present invention are typically angiosperms and preferably cultivated plants whose fruits are edible. Examples of such plants include, but are not limited to, plants belonging to Solanaceae such as tomato (*Solanum lycopersicum*), eggplant (*Solanum melongena*), and bell pepper (*Capsicum annuum* var. *grossum*); and Cucurbitaceae such as e.g., cucumber (*Cucumis sativus* L.), melon (*Cucumis melo* L.), watermelon (*Citrullus lanatus*), squash (*Cucurbita*), and oriental melon (*Cucumis melo* var. *makuwa*). Preferably, the plants used in the present invention are not parthenocarpic or have very low levels of parthenocarpy in the natural environment. A particularly preferred plant subject is tomato (tomato plant).

Any tomato can be used in the present invention. However, more preferred examples of tomatoes include, but are not limited to, tomato strains/varieties or derivatives thereof belonging to *Solanum lycopersicum, Solanum cerasiforme* (also known as *Lycopersicon cerasiforme*), *Solanum pimpinellifolium* (also known as *Lycopersicon Solanum cheesmanii* (also known as *Lycopersicon cheesmanii*), *Solanum parviflorum* (also known as *Lycopersicon parviflorum*), *Solanum chmielewskii* (also known as *Lycopersicon chmielewskii*), *Solanum hirsutum* (also known as *Lycopersicon hirsutum*), *Solanum pennellii* (also known as *Solanum Lycopersicon pennellii*), *Solanum peruvianum* (also known as *Solanum pennellii* or *Lycopersicon peruvianum*), *Solanum chilense* (also known as *Lycopersicon chilense*), *Solanum lycopersicoides, Solanum habrochaites* and the like. As one example of tomato, the wild type tomato variety Micro-Tom (*Solanum lycopersicum* cv. Micro-Tom) (Scott J W, Harbaugh B K (1989) Micro-Tom A miniature dwarf tomato, Florida Agr. Expt. Sta. Circ. 370, pp. 1-6) is commercially available, and it is also be available from the Tomato Genetics Resource Center (TGRC) (U.S.A.) under Accession No. LA3911. The wild type tomato variety Micro-Tom is a dwarf plant (approximately 10 to 20 cm in length) with small leaves and fruits, and it can also be crossed with a conventional tomato variety. The whole genome sequence has been determined for the wild type tomato variety Micro-Tom (Kobayashi M, et al., (2014) Plant Cell Physiol. 2014 February; 55(2): 445-454).

The term "derivative" used herein refers to a progeny plant obtained by crossing a parent plant with a different plant strain/variety at least one time or through mutagenesis or mutation introduction in a parent plant.

The cyclin F-box gene is a gene encoding a cyclin F-box protein (also referred to as "cyclin-type F-box protein") which is one of the F-box family proteins (a group of proteins each having a domain called "F-box region") involved in recognition and degradation of certain proteins. The cyclin F-box genes have been identified in various plants. For instance, examples of the nucleotide sequence of the tomato cyclin F-box gene and the amino acid sequence encoded by the nucleotide sequence are seen under Accession Nos. XM_004229918 and XP_004229966 in the database of the NCBI (National Center for Biotechnology Information, U.S.A.). The nucleotide sequence (CDS sequence) of the tomato wild type cyclin F-box gene and the amino acid sequence of the tomato wild type cyclin F-box protein encoded by the nucleotide sequence are set forth in SEQ ID NOs: 1 and 2, respectively. In addition, examples of the nucleotide sequence of the cyclin F-box gene and the amino acid sequence encoded by the nucleotide sequence of other plant species are as follows, with NCBI accession numbers: sweet orange (XM_006491151 and XP_006491214, XM_006491152 and XP_006491215, XM_006491153 and XP_006491216), apple (XM_008377812 and XP_008376034, XM_008377813 and XP_008376035), Chinese pear (XM_009378963 and XP_009377238), grape (XM_002276408 and XP_002276444, XM_010663560 and XP_010661862, XM_010663561 and XP_010661863, XM_010663562 and XP_010661864, and XM_010663563 and XP_010661865), cucumber (XM_004133777 and XP_004133825, XM_011652398 and XP_011650700), and melon (XM_008439705 and XP_008437927, XM_008439706 and XP_008437928, and XM_008439707 and XP_008437929). Other plant-derived homologous genes (homologs) to the tomato wild type cyclin F-box gene comprising the nucleotide sequence set forth in SEQ ID NO: 1 are also included in the scope of the cyclin F-box gene. In addition, the "CDS sequence" of the cyclin F-box gene means the nucleotide sequence of the cyclin F-box protein-coding region from the initiation codon to the termination codon.

Preferably, the mutant cyclin F-box gene comprising a gene function-altering mutation that confers parthenocarpy is an endogenous cyclin F-box gene in the plant genome, into which a gene function-altering mutation confers parthenocarpy has been introduced.

The term "gene" used herein encompasses DNA and RNA (e.g., mRNA). In the context of the present invention, a gene may consist of a protein-coding sequence (ranging from the initiation codon to the termination codon) and may further comprise the 5' untranslated region including the translation initiation site, the 3' untranslated region including the polyadenylation signal and/or the RNA-degradable regulatory region, or the like.

In the context of the present invention, a gene function-altering mutation that confers parthenocarpy in the mutant cyclin F-box gene means a nucleotide mutation that results in parthenocarpy as a result of functional alteration of the cyclin F-box gene. More specifically, the functional alteration of the cyclin F-box gene means a functional alteration (e.g., a change in protein conformation, activity, or properties such as degradability) of the cyclin F-box protein encoded by the cyclin F-box gene.

A gene function-altering mutation that confers parthenocarpy, which is present in the mutant cyclin F-box gene, may be, for example, a nucleotide mutation that causes deletion, substitution (preferably non-conservative substitution), insertion, or addition of 1 to 50, preferably 1 to 40, and more preferably 1 to 10, e.g., 1 to 5 amino acid residues in the amino acid sequence of the wild type cyclin F-box protein as long as it confers parthenocarpy.

One example of a mutant cyclin F-box gene used in the present invention that confers parthenocarpy is a cyclin F-box gene comprising, as a gene function-altering mutation that confers parthenocarpy, a nucleotide mutation that causes a non-conservative amino acid substitution of proline at position 398 defined based on the amino acid sequence set forth in SEQ ID NO: 2 (the amino acid sequence of the tomato wild type cyclin F-box protein) in the cyclin F-box protein. In other words, this mutant cyclin F-box gene encodes a cyclin F-box protein having a non-conservative amino acid substitution of proline at position 398 defined based on the amino acid sequence set forth in SEQ ID NO: 2. The non-conservative amino acid substitution of proline means a substitution of proline by an amino acid that has different properties from proline. Specifically, such substitution encompasses a substitution of proline (hydrophobic, non-polar amino acid) by a polar uncharged amino acid (serine, threonine, glutamine, asparagine, or cysteine), an aromatic amino acid (phenylalanine, tyrosine, or tryptophan), an acidic amino acid (polar charged; glutamic acid, or aspartic acid), or a basic amino acid (polar charged; lysine, arginine, or histidine). Alternatively, the substitution encompasses a substitution of proline (hydrophobic, non-polar amino acid) by polar amino acid or hydrophilic amino acid (serine, threonine, asparagine, glutamine, tyrosine, tryptophan, cysteine, lysine, arginine, histidine, aspartic acid, or glutamic acid). In one preferred embodiment, a non-conservative amino acid substitution of proline is a substitution of proline by glutamine. A nucleotide mutation that causes a substitution of proline by glutamine is, for example, a mutation from any of codons CCT, CCC, CCA, and CCG to codon CAA or CAG.

In the context of the present invention, the expression "proline at position 398 defined based on the amino acid sequence set forth in SEQ ID NO: 2" refers to proline in an arbitrary amino acid sequence (an amino acid sequence of any cyclin F-box protein) aligned with the amino acid sequence set forth in SEQ ID NO: 2, in which such proline is aligned with the proline at position 398 of SEQ ID NO: 2. Therefore, the "proline at position 398 defined based on the amino acid sequence set forth in SEQ ID NO: 2" may be proline at position 398 or proline at a position other than position 398 in an amino acid sequence of any cyclin F-box protein that is aligned with the amino acid sequence set forth in SEQ ID NO: 2. For example, in the cyclin F-box protein having one amino acid deletion near the N-terminus, the proline is located at position 397, but may be specified as "proline at position 398 defined based on the amino acid sequence set forth in SEQ ID NO: 2", provided that the proline is aligned with the proline at position 398 of SEQ ID NO: 2. In the present invention, the alignment between the amino acid sequence set forth in SEQ ID NO: 2 and the amino acid sequence of any cyclin F-box protein may have a gap and should be made such that differences between the sequences (e.g., insertion, deletion, substitution, or addition) are minimized, and the alignment achieves maximum match level. Similar expressions such as "(nucleotide) at position Y defined based on the nucleotide sequence set forth in SEQ ID NO: X" and "(amino acid) at position Y defined based on the amino acid sequence set forth in SEQ ID NO: X" should be understood in a similar manner.

The above-described mutant cyclin F-box gene that confers parthenocarpy may have 80% or more, preferably 90% or more, more preferably 95% or more, further preferably 98% or more, and particularly preferably 99% or more, e.g., 99.5% or more sequence identity to the amino acid sequence set forth in SEQ ID NO: 2 and encode an amino acid sequence comprising a non-conservative amino acid substitution of proline at position 398 defined based on the amino acid sequence set forth in SEQ ID NO: 2. This non-conservative amino acid substitution of proline is preferably a substitution of proline by a polar uncharged amino acid (serine, threonine, glutamine, asparagine, or cysteine), an aromatic amino acid (phenylalanine, tyrosine, or tryptophan), an acidic amino acid (glutamic acid, or aspartic acid), or a basic amino acid (lysine, arginine, or histidine); more preferably a substitution of proline by a polar amino acid or hydrophilic amino acid (serine, threonine, asparagine, glutamine, tyrosine, tryptophan, cysteine, lysine, arginine, histidine, aspartic acid, or glutamic acid); further preferably a substitution of proline by a polar uncharged amino acid (serine, threonine, glutamine, asparagine, or cysteine); and a particularly preferably a substitution of proline by glutamine. The above-described mutant cyclin F-box gene may be, but is not limited to, a mutant of the wild type cyclin F-box gene of preferably a plant of Solanaceae or Cucurbitaceae and more preferably tomato. In particular, the above-described mutant cyclin F-box gene may encode the amino acid sequence set forth in SEQ ID NO: 4. The amino acid sequence set forth in SEQ ID NO: 4 is an amino acid sequence having a substitution of proline at position 398 in the amino acid sequence set forth in SEQ ID NO: 2 (wild type tomato cyclin F-box protein) by glutamine. The present invention also provides such mutant cyclin F-box gene that confers parthenocarpy.

The mutant cyclin F-box gene may be a gene encoding an amino acid sequence derived from the amino acid sequence set forth in SEQ ID NO: 2 by deletion, substitution, insertion, or addition of 1 to 50, preferably 1 to 40, and more preferably 1 to 10, e.g., 1 to 5 amino acid residues as long as it encodes a mutant cyclin F-box protein that confers parthenocarpy. This mutant cyclin F-box gene contains a non-conservative amino acid substitution of proline at position 398 defined based on the amino acid sequence set forth in SEQ ID NO: 2, preferably by glutamine.

As long as the mutant cyclin F-box gene encodes a mutant cyclin F-box protein that confers parthenocarpy, the mutant gene may also comprise: (i) the nucleotide sequence set forth in SEQ ID NO: 3; or (ii) a nucleotide sequence having 70% or more, preferably 80% or more, more preferably 90% or more, further preferably 95% more, and particularly preferably 98% or more, e.g., 99% or more or 99.5% or more sequence identity to the nucleotide sequence set forth in SEQ ID NO: 1 and comprising a mutation from the codon CCA (encoding proline) at positions 1192 to 1194 defined based on the nucleotide sequence set forth in SEQ ID NO: 1 to the codon CAA or CAG (encoding glutamine). Such mutation may be, for example, a substitution of cytosine (C) at position 1193 defined based on the nucleotide sequence set forth in SEQ ID NO: 1 in the cyclin F-box gene by adenine (A). The mutant cyclin F-box gene may comprise the above-described nucleotide sequence as a protein-coding sequence (from the initiation codon to the termination codon).

In this description, sequence identity (%) to a specific amino acid sequence or nucleotide sequence means sequence identity (%) to the full length of the specific amino acid sequence or nucleotide sequence.

The plant according to the present invention is preferably homozygous for the mutant cyclin F-box gene that confers parthenocarpy. The mutant cyclin F-box gene that confers parthenocarpy according to the present invention is recessively inherited. It is also preferred that the plant according to the present invention, which has the mutant cyclin F-box gene that confers parthenocarpy, does not have a wild type cyclin F-box gene at a locus other than the locus of the mutant cyclin F-box gene, in the genome.

The plant according to the present invention, which has the mutant cyclin F-box gene that confers parthenocarpy, is parthenocarpic. That is, in that plant, even if pollination and fertilization do not occur and artificial parthenocarpic induction treatment such as plant hormone treatment is not performed, fruit-setting and enlargement of fruits take place. Thus, the present invention provides a method for producing a parthenocarpic plant comprising introducing a gene function-altering mutation that confers parthenocarpy, for example, a nucleotide mutation that causes a non-conservative amino acid substitution of proline at position 398 defined based on the amino acid sequence set forth in SEQ ID NO: 2 in the cyclin F-box protein, into the cyclin F-box gene (typically, an endogenous cyclin F-box gene) of a plant. The non-conservative amino acid substitution of proline is as described above, and it is particularly preferably a substitution of proline by glutamine.

The gene function-altering mutation that confers parthenocarpy can be introduced into the cyclin F-box gene in a plant by conventional methods. For instance, to introduce the above-described mutation into the cyclin F-box gene, site-specific mutagenesis methods or the like such as oligonucleotide-directed mutagenesis (ODM) and ZFN-mediated mutagenesis can be used. The oligonucleotide-directed mutagenesis (ODM) causes a mutation of interest in the genome via the cellular mismatch repair mechanism by introduction of a short oligonucleotide comprising a mutation of interest in a sequence homologous to a target gene (cyclin F-box gene) into plant cells. The ZFN-mediated mutagenesis employs zinc finger nuclease (ZFN) and a short oligonucleotide comprising a mutation of interest in a sequence homologous to a target gene. Alternatively, it is also possible to introduce the above-described mutation into the cyclin F-box gene in a plant via homologous recombination by introducing the mutant cyclin F-box gene or its nucleic acid fragment containing the mutation site, as a template DNA, into plant cells. The mutation may be introduced by random mutagenesis techniques. For instance, mutagenesis can be performed in a plant genome by treatment with chemical mutagens or radiation such as gamma ray, X ray, neutron, beta ray, ultraviolet ray, ion beams, and synchrotron. Examples of chemical mutagens include, but are not limited to, ethyl methanesulfonate (EMS), ethyleneimine (EI), methyl nitrosourea (MNU), ethyl nitorosourea (ENU), and sodium azide. For instance, mutagenesis can be performed by soaking seeds in an ethyl methanesulfonate (EMS) solution for a certain period of time for treatment (EMS mutagenesis). A plurality of random mutagenesis methods may be used in combination. The whisker method, particle gun method, electroporation method, polyethylene glycol (PEG) method, microinjection method, or the like can be employed to introduce an oligonucleotide or a nucleic acid fragment into plant cells.

It is also possible to introduce the above-described mutation into a progeny plant by crossing a mutant plant having the mutant cyclin F-box gene that confers parthenocarpy in the genome, with a different plant individual. Preferably, the obtained progeny plants are examined for the presence or absence of the mutant cyclin F-box gene that confers parthenocarpy and plant individuals having the mutant cyclin F-box gene are selected.

It can be determined by conventional methods whether or not the plant according to the present invention is parthenocarpic. For example, when plant individuals are grown and subjected to emasculation treatment before flowering in order to avoid pollination, the absence of fruit-setting (fruit formation) during the subsequent cultivation indicates that the plant is not parthenocarpic, and the presence of fruit-setting indicates that the plant is parthenocarpic. The emasculation treatment is a treatment for removing the male function of flowers in order to prevent self-pollination. Examples of the emasculation treatment include a removal of stamens from buds, a heat treatment for causing a loss of the function of pollens, and the like. The plant according to the present invention having the mutant cyclin F-box gene has, but is not limited to, a parthenocarpic rate of preferably 30% or more, more preferably 50% or more, and further preferably 60% or more. In the context of the present invention, the parthenocarpic rate is calculated as the proportion (%) of the number of fruit-setting (i.e., the number of fruits) over the number of emasculated flowers within the same individual or strain. According to this method, it is possible to impart parthenocarpy to plants in an easier manner. It is possible to modify a plant such that the plant becomes parthenocarpic or increase the level of parthenocarpy of the plant by imparting parthenocarpy to the plant.

The plant according to the present invention can acquire an ability to produce fruits having improved sugar contents due to the above-described mutation in the cyclin F-box gene (or the mutant cyclin F-box gene). Therefore, the present invention also provides a method for producing a plant having an improved sugar content in fruit, comprising introducing a gene function-altering mutation that confers parthenocarpy, for example, a nucleotide mutation causing a non-conservative amino acid substitution of proline at position 398 defined based on the amino acid sequence set forth in SEQ ID NO: 2 in the cyclin F-box protein, into the cyclin F-box gene of a plant. This non-conservative amino acid substitution of proline is as described above, and it is particularly preferably a substitution of proline by glutamine. The preferred plant is a plant whose fruits are edible. The plant is preferably of Solanaceae or Cucurbitaceae and particularly preferably tomato. The gene function-altering mutation that confers parthenocarpy is as described above.

The expression "having an improved sugar content in fruit" with respect to the plant according to the present invention means that the sugar contents in fruits produced by the plant according to the present invention are statistically significantly increased compared with wild type plant of the same variety or strain which has the wild type cyclin F-box gene (i.e., not having a gene function-altering mutation that confers parthenocarpy). The expression "plant having an improved sugar content in fruit" refers to a plant having an ability to produce fruits having improved sugar contents without a special treatment for achieving high sugar contents. Such plant includes not only a plant just bearing fruits having improved sugar contents, but also a plant which bore or will bear fruits having improved sugar contents or a part thereof (e.g., seeds, seedling, or fruits). The fruits having improved sugar contents encompass parthenocarpic fruits, and preferably encompass both fruits with seeds (fruits produced through pollination treatment; also referred to as pollinated fruits) and parthenocarpic fruits. The parthenocarpic fruits preferably also show higher levels of improvement in the sugar contents than those of fruits with seeds. The sugar contents in parthenocarpic fruits or fruits with seeds may be increased, but are not limited to, for example, 1.2-fold or higher, preferably 1.5-fold or higher, and more preferably 1.8-fold or higher, compared with wild type fruits. The sugar contents in fruits can be measured by conventional methods. However, in the present invention, the Brix value (%) of juice from fruits can be used as an indicator of sugar content. The Brix value can be measured by conventional methods, and generally measured using a sugar content meter (e.g., portable sugar content meter BX-1, Kyoto Electronics Manufacturing Co., Ltd., Japan; or portable refractometer N-20E, ATAGO, Japan). Fruits for which the sugar contents are measured are ripe fruits such as red ripe fruits in the case of tomato. Reportedly, the average sugar content (Brix value) for typical tomatoes produced in Japan (excluding fruity tomatoes having high sugar contents) is about 5%. According to the present method, it is possible to readily prepare a plant capable of producing high-sugar content fruits without performing treatments for achieving high-sugar contents such as stress load.

A parthenocarpic plant obtained by introducing a gene function-altering mutation that confers parthenocarpy, for example, a nucleotide mutation that causes a non-conservative amino acid substitution of proline at position 398 defined based on the amino acid sequence set forth in SEQ ID NO: 2 in the cyclin F-box protein, into the cyclin F-box gene of a plant; and progeny plants thereof maintaining the mutation are included in the scope of the parthenocarpic plant according to the present invention.

The plant according to the present invention, which has the above-described mutation in the cyclin F-box gene (mutant cyclin F-box gene that confers parthenocarpy), may also have a variety of changes in morphology or growth characteristics, compared with the wild type plant. For example, the plant according to the present invention may have changes in leaves or fruits (changes in leaf morphology, leaf color, fruit morphology, etc.). For instance, in contrast to leaves of common wild type tomato plants that are composed of a plurality of folioles having toothed (incised) edges, the tomato plant according to the present invention, which is a mutant of the wild type tomato plant, preferably develops leaves which have weaker-toothed edges (reduction of the depth and number of leaf teeth), fused folioles, increased leaf greenness compared to the wild type plant, or the like (see FIGS. 1 and 3). The leaf greenness can be estimated as leaf SPAD value (optical density of chlorophyll). The SPAD value can be calculated for a sample by conventional methods based on a difference in optical density between the red region which is absorbed by chlorophyll and the infrared region which is hardly absorbed by pigments. The SPAD value can be measured using a commercially available SPAD meter (chlorophyll meter) in a non-destructive manner. In the plant according to the present invention, the leaf greenness is increased compared with plants that do not have the above-described mutation at the same days old after seeding. Specifically, the SPAD value in the plant according to the present invention can be increased by, but is not limited to, preferably 10% or more and more preferably 20% or more.

In addition, the plant according to the present invention, which has the above-described mutation in the cyclin F-box gene (mutant cyclin F-box gene that confers parthenocarpy), may exhibit a reduction in the main stem length and the like compared with the wild type plant.

Further, the plant according to the present invention, which has the above-described mutation in the cyclin F-box gene (mutant cyclin F-box gene that confers parthenocarpy), may exhibit a decrease in the period of time required for formation of ripe fruits and/or an increase in the fruit pulp thickness, and the like compared with the wild type plant.

The plant according to the present invention, which has the above-described mutation in the cyclin F-box gene (mutant cyclin F-box gene that confers parthenocarpy), is parthenocarpic, but preferably has fertility, i.e., an ability to bear fruits via pollination and fertilization.

The present invention also relates to a method of plant breeding comprising crossing plants using a plant having the mutant cyclin F-box gene comprising the gene function-altering mutation that confers parthenocarpy (the plant according to the present invention) as a breeding parent, obtaining progeny plants and selecting a progeny plant having the mutant cyclin F-box gene introduced therein. The expression "crossing plants using the plant according to the present invention . . . as a breeding parent" refers to crossing the plants according to the present invention or crossing the plant according to the present invention with a plant of the same species or closely related species in order to introduce the above-described mutation in the cyclin F-box gene (mutant cyclin F-box gene that confers parthenocarpy) harbored by the plant according to the present invention into a progeny plant. Crossing may be carried out once or repeatedly. For instance, the plant according to the present invention may be crossed with a plant of the same species or closely related species (recurrent parent), then the resulting progeny plant crossed with the recurrent parent (backcrossing), and the further resulting progeny plant further crossed with the recurrent parent repeatedly (continuous backcrossing). Alternatively, the plant according to the present invention may be crossed with a plant of the same species or closely related species and then the resulting progeny plant crossed with a different plant of the same species or closely related species. The progeny plants of the plant according to the present invention may be self-crossed repeatedly to fix the above-described mutation and characteristics resulting from the mutation (e.g., parthenocarpy, increased sugar content in fruit, and leaf alteration) in the plant genome.

A progeny plant having the introduced mutant cyclin F-box gene (i.e., a progeny plant having the above-described mutation in the cyclin F-box gene) can be selected by detecting the mutant cyclin F-box gene in progeny plants. The mutant cyclin F-box gene can be detected by, for example, applying various well-known methods for detecting a nucleotide mutation, such as a method involving nucleic acid amplification and/or Southern hybridization etc., to a nucleic acid sample (e.g., genomic DNA, mRNA, or cDNA reverse-transcribed from mRNA) derived from the progeny plant. For instance, the presence or absence of the above-described mutation can be determined by performing nucleic acid amplification of a region including the above-described mutation of the cyclin F-box gene in the genome, determining the nucleotide sequence of an amplification product, and comparing the nucleotide sequence with the wild type genome sequence. Those skilled in the art can appropriately design primers used for such nucleic acid amplification based on the genome sequence of a target plant, e.g., the nucleotide sequence of the cyclin F-box gene and the position and type of the mutation introduced. Alternatively, the presence or absence of the above-described mutation in the progeny plant can also be determined based on the results of restriction enzyme cleavage by performing nucleic acid amplification using a primer set which is designed such that an amplification fragment comprising the above-described mutation is exclusively cleaved with a particular restriction enzyme while an amplification fragment from the wild type cyclin F-box gene is not cleaved with the restriction enzyme, and cleaving the amplification products with the restriction enzyme. One example of the primer set which is designed such that an amplification fragment comprising the above-described mutation is exclusively cleaved with a particular restriction enzyme while an amplification fragment from the wild type cyclin F-box gene is not cleaved with the restriction enzyme, is a primer set that comprises a primer comprising the nucleotide sequence set forth in SEQ ID NO: 5 (forward primer) and a primer comprising the nucleotide sequence set forth in SEQ ID NO: 6 (reverse primer). In a case where this primer set is used to amplify tomato plant-derived DNA (genomic DNA), an amplification product from a cyclin F-box gene having a substitution of cytosine (C) at position 1193 defined based on the nucleotide sequence set forth in SEQ ID NO: 1 by adenine (A), such as a mutant cyclin F-box gene having the nucleotide sequence set forth in SEQ ID NO: 3, is exclusively cleaved with the restriction enzyme NcoI, while an amplification product from the wild type cyclin F-box gene is not cleaved with the restriction enzyme NcoI. Therefore, in that case, the above-described mutant cyclin F-box gene in a progeny tomato plant can be detected based on, e.g., the results of restriction enzyme NcoI treatment of the amplification product obtained with the above primer set, followed by electrophoresis. Accordingly, the above primer set is useful for selection and discrimination of tomato plants having the introduced mutant cyclin F-box gene. The present invention also provides the above-described primers and primer set. The primers according to the present invention can be prepared by a chemical synthesis method well-known to those skilled in the art. For instance, the primers can be synthesized using a commercially available automated DNA synthesizer in accordance with commonly used procedures.

For example, the primers according to the present invention may comprise a labeling substance (e.g., a fluorescent molecule, a dye molecule, a radioactive isotope, or an organic compound such as digoxigenin or biotin) for facilitating detection or amplification of the primers and/or an additional sequence (e.g., a loop primer portion used in the LAMP method) at their 5' ends or 3' ends. The primers according to the present invention may be phosphorylated or aminated at their 5'ends. The primers according to the present invention may be DNA or RNA. In the case of RNA, "T (thymine)" in a DNA sequences shall be read as "U (uracil)" for specifying its nucleotide sequence. The present invention also provides a kit including the primer set according to the present invention. The kit may further include at least one selected from polymerases, restriction enzymes (e.g., NcoI), an instruction, and the like. This kit is also preferred for producing a parthenocarpic tomato plant and a plant having an improved sugar content in fruit. The kit is also preferred for breeding tomato plants.

Alternatively, the detection of the mutant cyclin F-box gene that confers parthenocarpy may be carried out by a method of determining the presence or absence of a mutation, comprising hybridizing an amplification product of a mutation-introduced region in the mutant cyclin F-box gene with an amplification product of the same region but having no mutation introduced therein in the wild type cyclin F-box gene to form a heteroduplex and detecting a mismatch site, which occurs as a result of introduction of a mutation, in a specific manner (e.g., detection based on mismatch site-specific cleavage with a nuclease or the like). The F-PHFA method based on the combination of competitive hybridization and fluorescence resonance energy transfer (FRET), a method involving hybridization with a probe that specifically binds to a region having the above-described mutation introduced therein or based on the combination of such hybridization and real-time PCR, and the like may also be used. A variety of the mutation detection methods described above can be carried out using commercially available products such as sequencer, PCR system, various mutation detection kits, and the like.

A progeny plant having the introduced mutant cyclin F-box gene that confers parthenocarpy can be also selected based on changes in morphology or growth characteristics of the progeny plant caused by introduction of the mutant cyclin F-box gene. For instance, regarding the plant according to the present invention, it is also possible to select a progeny plant based on changes in leaves. For example, in the case of a tomato plant, it is considered that leaves composed of a plurality of folioles having toothed (incised) edges indicates a phenotype of the wild type plant, and the development of leaves having weaker-toothed edges and fused folioles, compared with the wild type plant, indicates a phenotype of the mutant plant (a plant having the mutant cyclin F-box gene introduced therein). Therefore, the wild type plant and the mutant plant can be distinguished from each other based on differences in leaf morphology. The wild type tomato plant and the mutant plant can also be distinguished based on differences in leaf morphology of the tomato plant by determining the occurrence or non-occurrence of fusion of folioles. The deeper leaf greenness of a tomato plant (typically the SPAD value) than that of the wild type plant indicates a phenotype of the mutant plant. Therefore, distinguishing the wild type tomato plant and the mutant plant may be carried out based on a difference in leaf color as an indicator. Further, the above-described other changed phenotypes (e.g., an increased sugar content in fruit) which are exhibited by the plant according to the present invention due to the above-described mutation in the cyclin F-box gene, may be used as an indicator for selecting progeny plants. These other phenotypes may be used alone as an indicator for selection, but preferably used as an indicator in combination with detection of the mutant cyclin F-box gene or selection based on changes in leaves.

It is possible to breed a parthenocarpic plant by introducing the mutant cyclin F-box gene that confers parthenocarpy into a progeny plant as described above. In addition, it is possible to breed a plant having an improved sugar content in fruit by introducing the mutant cyclin F-box gene that confers parthenocarpy into a progeny plant. According to the breeding method of the present invention, it is possible to impart a variety of phenotypes of the mutant plants described above to a plant by introducing the mutant cyclin F-box gene that confers parthenocarpy into a progeny plant.

In the context of the present invention, the term "plant" basically includes various growth stages and various parts of a plant, such as a plant body, stems, leaves, roots, flowers, buds, fruits (fruit pulp or pericarp), seeds, tissues, cells, and callus. However, the term "plant" used in the present invention can refer to a plant body depending on the context, and those skilled in the art can readily understand what is meant by the term. The terms "tomato" and "tomato plant" used in the present invention basically includes various growth stages and various parts, such as a plant body, stems, leaves, roots, flowers, buds, fruits (fruit pulp or pericarp), seeds, seedlings, tissues, cells, and callus of a tomato, but the terms can refer to a tomato fruit and tomato plant body respectively, depending on the context and those skilled in the art can readily understand what are meant by the terms. In a preferred embodiment, the plant according to the present invention is, but is not limited to, a seed, fruit, seedling, or plant body.

It is possible to cultivate the plant according to the present invention without parthenocarpic induction treatment such as pollination treatment or plant hormone treatment, thereby inducing fruit-setting and obtaining fruits. The parthenocarpic induction treatment may be or may not be conducted upon cultivation of the plant according to the present invention. For the purpose of obtaining parthenocarpic fruits, the plant according to the present invention may be subjected to emasculation treatment before flowering. The emasculation treatment enables the avoidance of pollination, thereby obtaining parthenocarpic fruits with certainty. Cultivation can be carried out by any cultivation method such as hydroponic cultivation, facility cultivation (e.g., greenhouse cultivation or plant factory cultivation), open-field cultivation, or planter cultivation. The present invention also relates to a method for cultivating fruits, comprising cultivating the plant according to the present invention without parthenocarpic induction treatment.

In another embodiment, the present invention relates to a plant having a mutant cyclin F-box gene comprising a different gene-function-altering mutation that confers an improved sugar content in fruit; and a method for producing thereof. The plant according to the present invention has an improved sugar content in fruit, compared with a plant having the wild type cyclin F-box gene.

In the present invention, a target plant for the improvement of sugar content in fruit is as described above regarding a parthenocarpic plant, and particularly preferably tomato (a tomato plant).

The plant having an improved sugar content in fruit according to the present invention preferably has a gene-function-altering mutation which confers an improved sugar content in fruit introduced into the endogenous cyclin F-box gene in the plant genome.

An example of another mutant cyclin F-box gene that confers an improved sugar content in fruit as used in the present invention is a cyclin F-box gene, which has, as a gene function-altering mutation that confers an improved sugar content in fruit, a nucleotide mutation that causes a non-conservative amino acid substitution of serine at position 37 or glycine at position 301 defined based on the amino acid sequence set forth in SEQ ID NO: 2 in a cyclin F-box protein. The mutant cyclin F-box gene encodes a cyclin F-box protein having a non-conservative amino acid substitution of serine at position 37 or glycine at position 301 defined based on the amino acid sequence set forth in SEQ ID NO: 2.

The non-conservative amino acid substitution of serine at position 37 refers to a substitution of serine by an amino acid that has different properties from serine. Specifically, such substitution encompasses a substitution of serine (hydrophilic, polar uncharged amino acid) by an aliphatic amino acid (hydrophobic; alanine or glycine), a branched amino acid (hydrophobic; valine, leucine, or isoleucine), another hydrophobic amino acid (methionine, proline, phenylalanine, or tryptophan), an acidic amino acid (glutamic acid, or aspartic acid), or a basic amino acid (lysine, arginine, or histidine). In one preferred embodiment, the non-conservative amino acid substitution of serine is a substitution of serine (hydrophilic) by a hydrophobic amino acid (alanine, valine, leucine, isoleucine, methionine, proline, phenylalanine, tryptophan); more preferably by a branched amino acid (valine, leucine, or isoleucine); and further preferably by leucine. A nucleotide mutation that causes a substitution of serine by leucine is, for example, a mutation of any of the codons TCT, TCC, TCA, TCG, AGT and AGC into any of the codons TTA, TTG, CTT, CTC, CTA, and CTG.

The non-conservative amino acid substitution of glycine at position 301 refers to a substitution of glycine by an amino acid that has different properties from glycine. Specifically, such substitution encompasses a substitution of glycine (hydrophobic, non-polar amino acid) by a polar uncharged amino acid (serine, threonine, glutamine, asparagine, or cysteine), an aromatic amino acid (phenylalanine, tyrosine, or tryptophan), an acidic amino acid (glutamic acid or aspartic acid), or a basic amino acid (lysine, arginine, or histidine). In one preferred embodiment, a non-conservative amino acid substitution of glycine is a substitution of glycine (hydrophobic, non-polar amino acid) by a polar amino acid or hydrophilic amino acid (serine, threonine, asparagine, glutamine, tyrosine, tryptophan, cysteine, lysine, arginine, histidine, aspartic acid, or glutamic acid); more preferably by a basic amino acid (lysine, arginine, or histidine); and further preferably by arginine. A nucleotide mutation that causes a substitution of glycine by arginine is, for example, a mutation of any of the codons GGT, GGC, GGA, and GGG into any of the codons CGT, CGC, CGA, CGG, AGA, and AGG.

In the context of the present invention, the expression "serine at position 37 defined based on the amino acid sequence set forth in SEQ ID NO: 2" or "glycine at position 301 defined based on the amino acid sequence set forth in SEQ ID NO: 2" refers to serine or glycine which is aligned with serine at position 37 or glycine at position 301 of SEQ ID NO: 2, respectively, in an arbitrary amino acid sequence (an amino acid sequence of any cyclin F-box protein) aligned with the amino acid sequence set forth in SEQ ID NO: 2.

The mutant cyclin F-box gene that confers an improved sugar content in fruit may have 80% or more, preferably 90% or more, more preferably 95% or more, further preferably 98% or more, and particularly preferably 99% or more, e.g., 99.5% or more sequence identity to the amino acid sequence set forth in SEQ ID NO: 2 and encode an amino acid sequence comprising a non-conservative amino acid substitution of serine at position 37 defined based on the amino acid sequence set forth in SEQ ID NO: 2. This non-conservative amino acid substitution of serine may be a substitution of serine by an amino acid that has different properties from serine, such as an aliphatic amino acid (hydrophobic; alanine or glycine), a branched amino acid (hydrophobic; valine, leucine, or isoleucine), another hydrophobic amino acid (methionine, proline, phenylalanine, or tryptophan), an acidic amino acid (glutamic acid or aspartic acid), or a basic amino acid (lysine, arginine, or histidine); more preferably a substitution of serine by a hydrophobic amino acid (alanine, valine, leucine, isoleucine, methionine, proline, phenylalanine, or tryptophan); further preferably a substitution of serine by a branched amino acid (valine, leucine, or isoleucine); or a particularly preferably a substitution of serine by leucine. The above-described mutant cyclin F-box gene may be, but is not limited to, a mutant of the wild type cyclin F-box gene of preferably a plant of Solanaceae or Cucurbitaceae, and more preferably of tomato. In particular, the above-described mutant cyclin F-box gene may encode the amino acid sequence set forth in SEQ ID NO: 20. The amino acid sequence set forth in SEQ ID NO: 20 is an amino acid sequence having a substitution of serine at position 37 in the amino acid sequence set forth in SEQ ID NO: 2 (wild type tomato cyclin F-box protein) by leucine. The present invention also provides such mutant cyclin F-box gene that confers an improved sugar content in fruit.

The mutant cyclin F-box gene that confers an improved sugar content in fruit may have 80% or more, preferably 90% or more, more preferably 95% or more, further preferably 98% or more, and particularly preferably 99% or more, e.g., 99.5% or more sequence identity to the amino acid sequence set forth in SEQ ID NO: 2 and encode an amino acid sequence comprising a non-conservative amino acid substitution of glycine at position 301 defined based on the amino acid sequence set forth in SEQ ID NO: 2. This non-conservative amino acid substitution of glycine may be a substitution of glycine by an amino acid that has different properties from glycine, such as a polar uncharged amino acid (serine, threonine, glutamine, asparagine, or cysteine), an aromatic amino acid (phenylalanine, tyrosine, or tryptophan), an acidic amino acid (glutamic acid or aspartic acid), or a basic amino acid (lysine, arginine, or histidine); more preferably a substitution of glycine by a polar amino acid or a hydrophilic amino acid (serine, threonine, asparagine, glutamine, tyrosine, tryptophan, cysteine, lysine, arginine, histidine, aspartic acid, or glutamic acid); further preferably a substitution of glycine by a basic amino acid (lysine, arginine, or histidine); and particularly preferably a substitution of glycine by arginine. The mutant cyclin F-box gene may be, but is not limited to, preferably a mutant of the wild type cyclin F-box gene of a plant of Solanaceae or Cucurbitaceae, and more preferably of tomato. In particular, the above-described mutant cyclin F-box gene may encode the amino acid sequence set forth in SEQ ID NO: 22. The amino acid sequence set forth in SEQ ID NO: 22 is an amino acid sequence having a substitution of glycine at position 301 in the amino acid sequence set forth in SEQ ID NO: 2 (wild type tomato cyclin F-box protein) by arginine. The present invention also provides such mutant cyclin F-box gene that confers an improved sugar content in fruit.

The mutant cyclin F-box gene that confers an improved sugar content in fruit may encode an amino acid sequence derived from the amino acid sequence set forth in SEQ ID NO: 2 by deletion, substitution, insertion, or addition of 1 to 50, preferably 1 to 40, and more preferably 1 to 10, e.g., 1 to 5 amino acid residues as long as it encodes a mutant cyclin F-box protein that confers the increase in the sugar content in fruit. Such mutant cyclin F-box gene may contain a non-conservative amino acid substitution of serine at position 37 or glycine at position 301 defined based on the amino acid sequence set forth in SEQ ID NO: 2.

The above-described mutant cyclin F-box gene that confers an improved sugar content in fruit may comprise: (i) the nucleotide sequence set forth in SEQ ID NO: 19; or (ii) a nucleotide sequence having 70% or more, preferably 80% or more, more preferably 90% or more, further preferably 95% more, and particularly preferably 98% or more, e.g., 99% or more or 99.5% or more sequence identity to the nucleotide sequence set forth in SEQ ID NO: 1 and comprising a mutation from the codon TCA (encoding serine) at positions 109 to 111 defined based on the nucleotide sequence set forth in SEQ ID NO: 1 to the codon TTA, TTG, CTT, CTC, CTA, or CTG (encoding leucine), as long as the mutant gene encodes a mutant cyclin F-box protein that confers an improved sugar content in fruit. Such mutation may be, for example, a substitution of cytosine (C) at position 110 defined based on the nucleotide sequence set forth in SEQ ID NO: 1 in the cyclin F-box gene by thymine (T). The mutant cyclin F-box gene may comprise the above-described nucleotide sequence as a protein-coding sequence (from the initiation codon to the termination codon).

Alternatively, the above-described mutant cyclin F-box gene that confers an improved sugar content in fruit may comprise: (i) the nucleotide sequence set forth in SEQ ID NO: 22; or (ii) a nucleotide sequence having 70% or more, preferably 80% or more, more preferably 90% or more, further preferably 95% more, and particularly preferably 98% or more, e.g., 99% or more or 99.5% or more sequence identity to the nucleotide sequence set forth in SEQ ID NO: 1 and comprising a mutation from the codon GGG (encoding glycine) at positions 901 to 903 defined based on the nucleotide sequence set forth in SEQ ID NO: 1 to the codon CGT, CGC, CGA, CGG, AGA, or AGG (encoding leucine), as long as the mutant gene encodes a mutant cyclin F-box protein that confers an improved sugar content in fruit. Such mutation may be, for example, a substitution of guanine (G) at position 901 defined based on the nucleotide sequence set forth in SEQ ID NO: 1 in the cyclin F-box gene by adenine (A). The mutant cyclin F-box gene may comprise the above-described nucleotide sequence as a protein-coding sequence (from the initiation codon to the termination codon).

The gene function-altering mutation that confers an improved sugar content in fruit can be introduced into the cyclin F-box gene in a plant by conventional methods. Specific embodiments of the method are as described above for the introduction of a mutation that confers parthenocarpy. The present invention also provides a method for producing a plant having an improved sugar content in fruit, comprising introducing a gene function-altering mutation that confers an improved sugar content in fruit, for example, a nucleotide mutation that causes a non-conservative amino acid substitution of serine at position 37 or glycine at position 301 defined based on the amino acid sequence set forth in SEQ ID NO: 2 in the cyclin F-box protein, into the cyclin F-box gene in a plant. According to this method, it is possible to readily prepare a plant capable pf producing high-sugar content fruits without performing treatments for achieving high-sugar contents such as stress load.

The plant having an improved sugar content in fruit according to the present invention is preferably homozygous for the mutant cyclin F-box gene that confers an improved sugar content in fruit.

It is also possible to introduce the above-described mutation into a progeny plant by crossing a mutant plant having the mutant cyclin F-box gene that confers an improved sugar content in fruit in the genome, with a different plant individual. Preferably, the obtained progeny plants are examined for the presence or absence of the mutant cyclin F-box gene that confers an improved sugar content in fruit and plant individuals having the mutant cyclin F-box gene are selected.

Whether the mutant cyclin F-box gene confers an improved sugar content in fruit can be examined by introducing the mutation in the mutant cyclin F-box gene into the endogenous cyclin F-box gene in a plant, measuring the sugar content in pollinated fruits (preferably ripe fruits) of the resulting plant mutant, and comparing the sugar content with the sugar content in pollinated fruits (preferably ripe fruits) of the wild type plant measured in the same manner. If the sugar content is increased (statistically significantly increased) compared with the wild type plant, it can be determined that the mutant cyclin F-box gene having the mutation confers an improved sugar content in fruit. Further, whether a plant having the mutant cyclin F-box gene has an improved sugar content in fruit may be determined by measuring the sugar content in pollinated fruits (preferably ripe fruits) of the plant and comparing the sugar content with the sugar content in pollinated fruits (preferably ripe fruits) of the wild type plant measured in the same manner, thereby confirming whether or not there is an increase in the sugar content. The sugar contents in fruits can be measured by conventional methods. However, in the present invention, the Brix value (%) of juice from fruits can be used as an indicator of sugar content. The Brix value can be measured using a sugar content meter (e.g., portable sugar content meter BX-1; Kyoto Electronics Manufacturing Co., Ltd., Japan; or portable refractometer N-20E, ATAGO, Japan).

The term "wild type" relating to a mutation that confers an improved sugar content in fruit means that the cyclin F-box gene does not have a mutation that confers an improved sugar content in fruit. The plant having a mutant cyclin F-box gene that confers an improved sugar content in fruit may be or may not be parthenocarpic while having an improved sugar content in fruit. The definition of the "plant having an improved sugar content in fruit" is as described above.

A plant having an improved sugar content in fruit obtained by introducing a gene function-altering mutation that confers an improved sugar content in fruit, such as a nucleotide mutation that causes a non-conservative amino acid substitution of proline at position 398, serine at position 37, or glycine at position 301 defined based on the amino acid sequence set forth in SEQ ID NO: 2 in the cyclin F-box protein, into the cyclin F-box gene in a plant; and a progeny plant maintaining the mutation are included in the scope of the plant having an improved sugar content in fruit according to the present invention.

The plant according to the present invention, which has a mutation that confers an improved sugar content in fruit in the cyclin F-box gene, may also have a variety of changes in morphology or growth characteristics, compared with the wild type plant. For example, the plant according to the present invention may have changes in leaves or fruits. For instance, in contrast to leaves of common wild type tomato plants that are composed of a plurality of folioles having toothed (incised) edges, the tomato plant according to the present invention, which has mutant cyclin F-box gene that confers an improved sugar content in fruit, preferably may have abnormalities in leaf morphology such as weaker-toothed leaf edges (reduction of the depth and number of leaf teeth) and fused folioles. A particularly strong leaf morphologic abnormality can be seen in a tomato plant having a mutant cyclin F-box gene comprising a nucleotide mutation that causes a non-conservative amino acid substitution of proline at position 398 or glycine at position 301 based on the amino acid sequence set forth in SEQ ID NO: 2.

The present invention also relates to a method of plant breeding, comprising crossing plants using a plant having the mutant cyclin F-box gene comprising the gene function-altering mutation that confers an improved sugar content in fruit as a breeding parent, obtaining progeny plants and selecting a progeny plant having the mutant cyclin F-box gene introduced therein. The expression "crossing plants using the plant according to the present invention . . . as a breeding parent" in the context of the plant having an improved sugar content in fruit refers to crossing the plants according to the present invention or crossing the plant according to the present invention with a plant of the same species or closely related species in order to introduce the above-described mutation (mutant cyclin F-box gene that confers an improved sugar content in fruit) in the cyclin F-box gene of the plant having an improved sugar content in fruit into a progeny plant. Crossing may be carried out once or repeatedly. For instance, the plant according to the present invention may be crossed with a plant of the same species or closely related species (recurrent parent), then the resulting progeny plant crossed with the recurrent parent (backcrossing), and the further resulting progeny plant further crossed with the recurrent parent repeatedly (continuous backcrossing). Alternatively, the plant according to the present invention may be crossed with a plant of the same species or closely related species and then the resulting progeny plant crossed with a different plant of the same species or closely related species. The progeny plants of the plant according to the present invention may be self-crossed repeatedly to fix the above-described mutation and an improved sugar content in fruit resulting from the mutation in the plant genome.

A progeny plant having the introduced mutant cyclin F-box gene that confers an improved sugar content in fruit (i.e., a progeny plant having the above-described mutation in the cyclin F-box gene) can be selected by detecting the mutant cyclin F-box gene in progeny plants. Detection of the mutant cyclin F-box gene is as described above for the detection of the mutant cyclin F-box gene that confers parthenocarpy. The presence or absence of the above-described mutation in the progeny plant can also be determined based on the results of restriction enzyme cleavage by performing nucleic acid amplification using a primer set which is designed such that an amplification fragment from the mutant cyclin F-box gene that confers an improved sugar content in fruit is exclusively cleaved with a particular restriction enzyme while an amplification fragment from the wild type cyclin F-box gene is not cleaved with the restriction enzyme, and cleaving the amplification products with the restriction enzyme. One example of such primer set is a primer set that comprises a primer comprising the nucleotide sequence set forth in SEQ ID NO: 15 (forward primer) and a primer comprising the nucleotide sequence set forth in SEQ ID NO: 16 (reverse primer). In a case where this primer set is used to amplify tomato plant-derived DNA (genomic DNA), an amplification product from a cyclin F-box gene having a substitution of guanine (G) at position 901 defined based on the nucleotide sequence set forth in SEQ ID NO: 1 by adenine (A), such as a mutant cyclin F-box gene having the nucleotide sequence set forth in SEQ ID NO: 21, is exclusively cleaved with the restriction enzyme BsaXI, while an amplification product from the wild type cyclin F-box gene is not cleaved with the restriction enzyme BsaXI. Therefore, in that case, the above-described mutant cyclin F-box gene in a progeny tomato plant can be detected based on, e.g., the results of restriction enzyme BsaXI treatment of the amplification product obtained with the above primer set, followed by electrophoresis. Another example of the primer set is a primer set that comprises a primer comprising the nucleotide sequence set forth in SEQ ID NO: 17 (forward primer) and a primer comprising the nucleotide sequence set forth in SEQ ID NO: 18 (reverse primer). In a case where this primer set is used to amplify tomato plant-derived DNA (genomic DNA), an amplification product from a cyclin F-box gene having a substitution of cytosine (C) at position 110 defined based on the nucleotide sequence set forth in SEQ ID NO: 1 by thymine (T), such as a mutant cyclin F-box gene having the nucleotide sequence set forth in SEQ ID NO: 19, is exclusively cleaved with the restriction enzyme XspI, while an amplification product from the wild type cyclin F-box gene is not cleaved with the restriction enzyme XspI. Therefore, in that case, the above-described mutant cyclin F-box gene in a progeny tomato plant can be detected based on, e.g., the results of restriction enzyme XspI treatment of the amplification product obtained with the above primer set, followed by electrophoresis. Accordingly, the above primer sets are useful for selection and discrimination of tomato plants having the introduced mutant cyclin F-box gene. The present invention also provides the above-described primers and primer sets. The primers according to the present invention can be prepared by a chemical synthesis method well-known to those skilled in the art. For instance, the primers can be synthesized using a commercially available automated DNA synthesizer in accordance with commonly used procedures. For example, primers according to the present invention may comprise a labeling substance (e.g., a fluorescent molecule, a dye molecule, a radioactive isotope, or an organic compound such as digoxigenin or biotin) for facilitating detection or amplification of the primers and/or an additional sequence (e.g., a loop primer portion used in the LAMP method) at their 5' ends or 3' ends. The primers according to the present invention may be phosphorylated or aminated at their 5'ends. The primers according to the present invention may be DNA or RNA. In the case of RNA, "T (thymine)" in a DNA sequence shall be read as "U (uracil)" for specifying its nucleotide sequence. The present invention also provides a kit including the primer set according to the present invention. The kit may further include at least one selected from polymerases, restriction enzymes (e.g., BsaXI or XspI), an instruction, and the like. This kit is preferred for producing a plant having an improved sugar content in fruit. The kit is also preferred for breeding tomato plants.

Alternatively, the detection of the mutant cyclin F-box gene that confers an improved sugar content in fruit may be carried out by a method of determining the presence or absence of a mutation, comprising hybridizing an amplification product of a mutation-introduced region in the mutant cyclin F-box gene with an amplification product of the same region but having no mutation introduced therein in the wild type cyclin F-box gene to form a heteroduplex and detecting a mismatch site, which occurs as a result of introduction of a mutation, in a specific manner (e.g., detection based on mismatch site-specific cleavage with a nuclease or the like). The F-PHFA method based on the combination of competitive hybridization and fluorescence resonance energy transfer (FRET), a method involving hybridization with a probe that specifically binds to a region having the above-described mutation introduced therein or based on the combination of such hybridization and real-time PCR, and the like may also be used. A variety of the mutation detection methods described above can be carried out using commercially available products such as sequencer, PCR system, various mutation detection kits, and the like.

A progeny plant having the introduced mutant cyclin F-box gene that confers an improved sugar content in fruit can be also selected based on changes in morphology or growth characteristics of the progeny plant caused by introduction of the mutant cyclin F-box gene. For example, regarding the plant according to the present invention, it is also possible to select a progeny plant based on a leaf morphologic abnormality. Such changes may be used alone as an indicator for selection, but preferably used as an indicator in combination with detection of the mutant cyclin F-box gene.

It is possible to breed a plant having an improved sugar content in fruit by introducing the mutant cyclin F-box gene that confers an improved sugar content in fruit into a progeny plant as described above.

The definition and explanation of the term "plant" in the context of the plant having an improved sugar content in fruit is as described above for the parthenocarpic plant.

The cyclin F-box gene is involved in e.g., fruit and leaf formation. In particular, a non-conservative amino acid substitution (e.g., a substitution between a hydrophobic amino acid and a hydrophilic amino acid) in the cyclin F-box gene in the plant genome may result in an improved sugar content in fruit by modifying the function of the cyclin F-box protein. Thus, the present invention provides a method for screening for a plant having an improved sugar content in fruit, comprising introducing a nucleotide mutation that causes a non-conservative amino acid substitution into the cyclin F-box gene in a plant and selecting a plant having an improved sugar content in fruit compared with wild type plant. A nucleotide mutation that causes a non-conservative amino acid substitution can be introduced at any site of the endogenous (genomic) cyclin F-box gene in a plant. The introduction of a nucleotide mutation that causes a non-conservative amino acid substitution can be performed as described above. A plant having the introduced mutation is cultivated, fruits thereof are obtained, and the sugar content in fruit is measured. A plant having the introduced mutation preferably bears homozygously the mutation (mutant cyclin F-box gene). The sugar content in fruit can be measured for pollinated fruits (fruits with seeds) or parthenocarpic fruits. The measurement of the sugar content in fruit and the comparison with the sugar content in fruit of the wild type plant can be performed as described above. If the sugar content is increased (statistically significantly increased) compared with the sugar content in pollinated fruits (preferably ripe fruits) of the wild type plant as measured in the same manner, it can be determined that the plant having a nucleotide mutation which causes the non-conservative amino acid substitution or the mutant cyclin F-box gene comprising such mutation confers an improved sugar content in fruit. Based on the determination, it possible to select a plant having an improved sugar content in fruit.

The present method also preferably comprises verifying introduction of a nucleotide mutation that causes a non-conservative amino acid substitution into the cyclin F-box gene. For instance, introduction of a nucleotide mutation that causes a non-conservative amino acid substitution into the cyclin F-box gene may be confirmed by sequencing the cyclin F-box gene of a plant into which the mutation has been introduced, and then the sugar content in fruit for a plant confirmed to have the introduced mutation may be determined. Cultivation, collecting fruits and measurement of the sugar content in fruit in the above-described manner only for plant individuals that have been confirmed to have the mutant cyclin F-box gene, can result in more efficient test processes. According to the screening method of the present invention, plants having an improved sugar content in fruit due to any of various non-conservative amino acid mutations in the cyclin F-box gene can be efficiently obtained.

EXAMPLES

The present invention will be specifically described in the following examples. However, these examples are not intended to limit the scope of the present invention.

[Example 1] Production of Tomato Mutant Strains and Selection of Parthenocarpic Tomato Strains EMS treatment (EMS mutagenesis treatment) was conducted by allowing 3000 seeds of the wild type tomato variety Micro-Tom (*Solanum lycopersicum* cv. Micro-Tom) to absorb sterile water at room temperature for 4 hours and then soaking the seeds in 100 ml of 1.0% ethyl methanesulfonate (EMS) solution with stirring for 16 hours. The seeds were taken out from the EMS solution and washed with 100 ml of sterile water for 4 hours with stirring. This washing process was repeated 3 times. Then, the seeds were allowed to germinate on filter paper moistened with sterile water and cultivated in a glass greenhouse. M2 seeds were formed by self-pollination from each strain (M1 generation) and collected. Ten M2 seeds per strain were sown and cultivated in connected pots containing culture soil in a glass greenhouse. Thus, Micro EMS-mutagenized population of tomato plants was obtained. Individuals (strains) showing high fruit-setting rates were selected from among the M2 strains and seeds were collected from each of the selected strains.

The collected seeds were sown on filter paper moistened with sterile water, and germinating seeds were settled on rockwool (mini block; size: 50 cm×50 cm×50 cm, Grodan) for cultivation. Cultivation was conducted in a plant factory at 25° C. with a day length of 16 hours (16 hours light and 8 hours dark per day). Irrigation was conducted by circulating a nutrient solution prepared from nutriculture fertilizers OAT House 1 and OAT House 2 (OAT Agrio Co., Ltd.) at an electric conductivity (EC) of approximately 1.5 ms/cm once a day during cultivation.

Cultivated plant individuals of each strain were examined by parthenocarpic test to determine the parthenocarpic rate. In the parthenocarpic test, emasculation treatment was conducted before flowering, and then the number of fruit-setting (i.e., the number of fruits) was examined. The parthenocarpic rate (%) was calculated as the proportion of the number of fruit-setting over the number of emasculated flowers within the same strain.

As a result, one strain showed a high parthenocarpic rate of 67%. This strain, E8986 strain, was selected as a parthenocarpic mutant strain and used for further analysis. Specifically, the growth characteristics, fruit characteristics, and hereditary nature of this parthenocarpic mutant strain were examined and mapping of causative genes were conducted in the following Examples.

[Example 2] Growth Characteristics of the Parthenocarpic Tomato Mutant Strain

Seeds of the parthenocarpic tomato mutant strain (E8986 strain) selected in Example 1 and the wild type tomato variety Micro-Tom (*Solanum lycopersicum* cv. Micro-Tom) (22 and 24 seeds, respectively) were used for comparing the strains in terms of growth characteristics. The significant difference between the obtained data of the treatment groups was tested with the Tukey-kramer HSD test.

The seeds were allowed to absorb sterile water for 3 days. The seeds after water absorption for 3 days were settled on Rockwool (mini block; size: 50 cm×50 cm×50 cm, Grodan) and cultivated in a plant factory at 25° C. with a day length of 16 hours until 8 weeks after settled planting. Irrigation was conducted by circulating a nutrient solution (Otsuka House A formulation) prepared from nutriculture fertilizers OAT House 1 and OAT House 2 at an electric conductivity (EC) of approximately 1.5 ms/cm once a day during cultivation.

Figure 2:
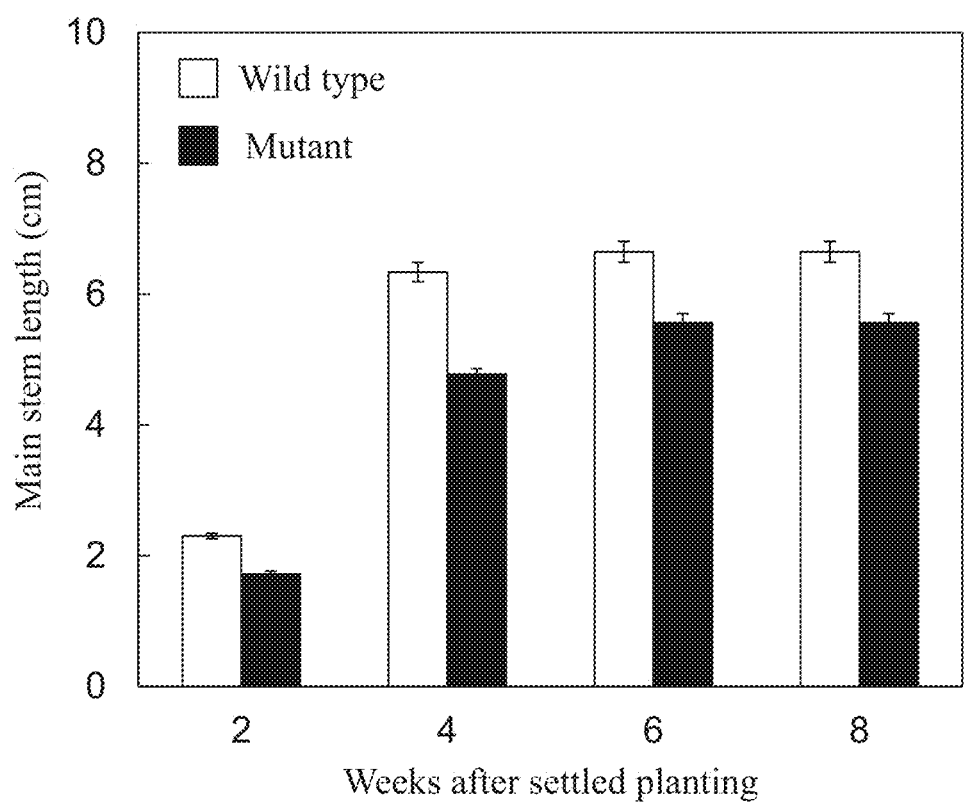
FIG. 2 shows the main stem length for wild type and mutant tomato plants.
Figure 3:
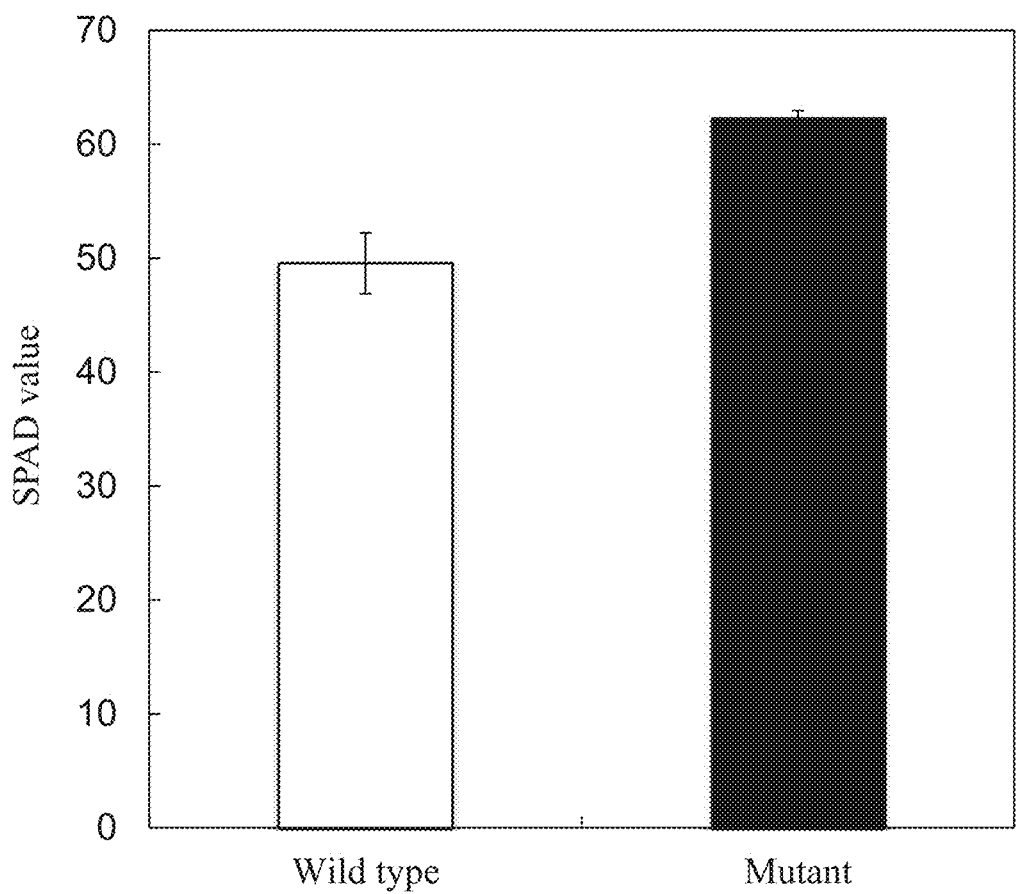
FIG. 3 shows the SPAD value of leaves for wild type and mutant tomato plants.

After settled planting, the main stem length was examined every 2 weeks over 8 weeks. The leaf SPAD value (i.e., the index value of chlorophyll content) was also examined 8 weeks after settled planting. The SPAD value was measured using a chlorophyll meter (SPAD-502 Plus, Konica Minolta, Inc.) 8 weeks after settled planting. The SPAD value was determined for the first to third leaves at apex of main stem, and the mean thereof was calculated. Further, leaf morphology was observed. FIGS. 1 to 3 show the results.

The parthenocarpic mutant strain was found to have characteristic leaf morphology. The wild type strain had toothed leaves, while the mutant strain had leaves having less sharp-toothed edges and the morphology thereof showed fusion of folioles (FIG. 1).

Compared with the wild type strain, the growth of the mutant strain already began to decrease in terms of the main stem length 2 weeks after settled planting, and the mean main stem length was 6.6 cm for the wild type strain and 5.6 cm for the mutant strain 8 weeks after settled planting (FIG. 2). It was shown that the main stem length of the mutant strain was statistically significantly shorter than that of the wild type strain at each examined week (FIG. 2). As the mutant strain has a shorter main stem length, it would be more convenient for a work of training stems. In addition, the leaf SPAD value (mean) of the mutant strain showed a statistically significantly higher value than that of the wild type strain, indicating that the leaf color of the mutant strain was dark (FIG. 3).

[Example 3] Fruit Characteristics of the Parthenocarpic Tomato Mutant Strain

Plant individuals of the parthenocarpic tomato mutant strain (mutant) selected in Example 1 and the wild type tomato variety Micro-Tom (wild type) (13 and 10 individuals, respectively) were cultivated for comparing the strains in terms of fruit characteristics. The significant difference between the obtained data of the treatment groups was tested with the Tukey-kramer HSD test.

The wild type and mutant strains were subjected to pollination treatment after flowering, or emasculation treatment before flowering. Pollination treatment was conducted by vibrating flowers using a vibrator (vibration pollination). The number of fruits was restricted to two per flower truss, and excess fruits were removed. Fruits with entirely red pericarp (i.e., red ripe fruits) were collected and immediately examined for fruit characteristics. For examination of fruit characteristics, the fruit-setting rate/parthenocarpic rate, fruit pulp thickness, Brix value (sugar content index), and the number of seeds were determined. The fruit-setting rate in the case of pollination treatment was calculated as the proportion (%) of the sum of the number of fruits with seeds and the number of seedless fruits (parthenocarpic fruits) over the number of blooming flowers. The parthenocarpic rate in this case was calculated as the proportion (%) of the number of seedless fruits (parthenocarpic fruits) over the number of pollinated flowers. The fruit-setting rate in the case of emasculation treatment, which corresponds to the parthenocarpic rate, was calculated as the proportion (%) of the number of fruit-setting over the number of emasculated flowers. The Brix value was measured for collected fruit juice using a sugar content meter (portable sugar content meter, BX-1, KEM). Regarding fruit pulp thickness, the Brix value, and the number of seeds, the mean value of all red ripe fruits collected from each individual was calculated, and then the mean value of the individuals for each group was further calculated.

In the wild type strain treatment group and the mutant strain treatment group, the mean fruit-setting rate was 91.7% for the wild type strain subjected to pollination treatment and 0% for the wild type strain subjected to emasculation treatment, while the mean fruit-setting rate was 84% for the mutant strain subjected to pollination treatment (fruits with seeds: 81%; and parthenocarpic fruits: 3%) and 64% for the mutant strain subjected to emasculation treatment. These results showed that the parthenocarpic rate of the mutant strain exceeds approximately 60%.

The numbers of days required from pollination treatment or emasculation treatment to formation of red ripe fruits were 50±1.2 days, 46±1.0 days, and 33±0.5 days (mean±standard error) for the wild type strain subjected to pollination treatment, the mutant strain subjected to pollination treatment, and the mutant strain subjected to emasculation treatment, respectively. It was shown that fruits formed in the mutant strain subjected to emasculation treatment (parthenocarpic fruits) become red ripe fruits with a statistically significantly fewer number of days, compared with the wild type strain and the mutant strain subjected to pollination treatment.

Figure 4:
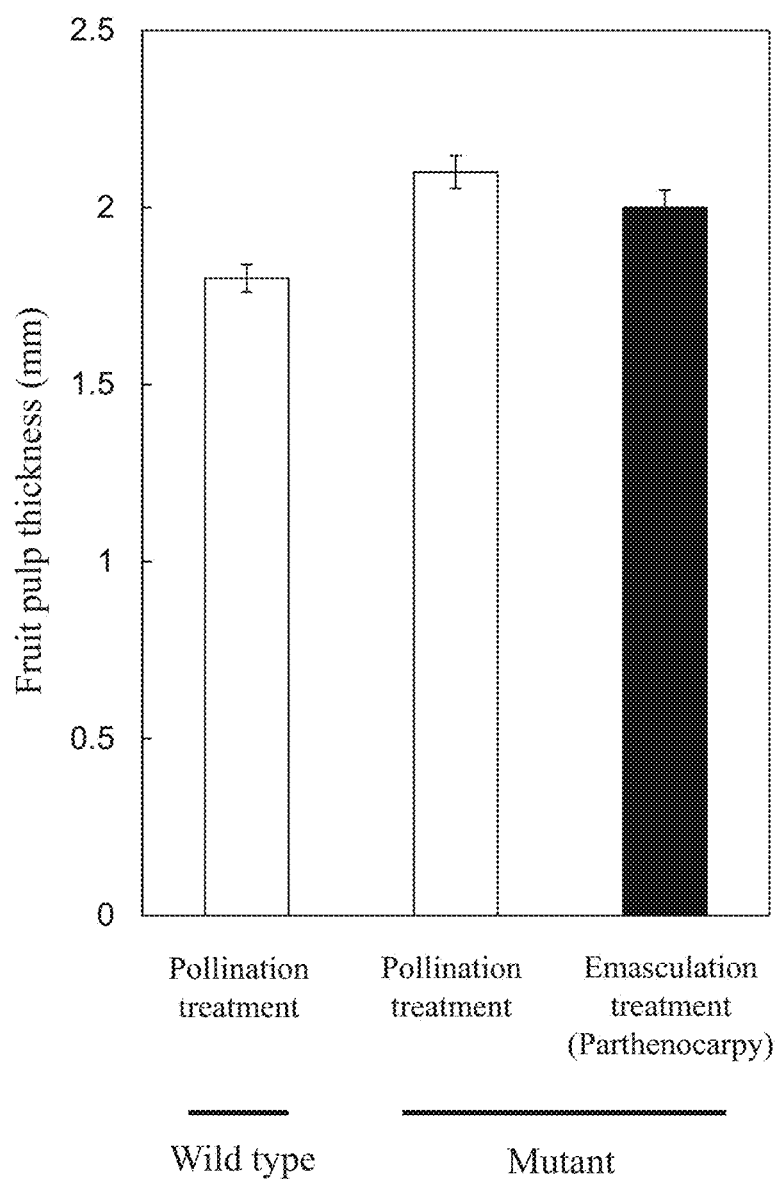
FIG. 4 shows the fruit pulp thickness (mm) for wild type and mutant tomato plants.

There was a difference in fruit pulp thickness as well. It was shown that the fruit pulp thickness of fruits of the mutant strain subjected to pollination treatment and that of fruits of the mutant strain subjected to emasculation treatment were statistically significantly greater than that of fruits of the wild type strain subjected to pollination treatment (FIG. 4).

Figure 5:
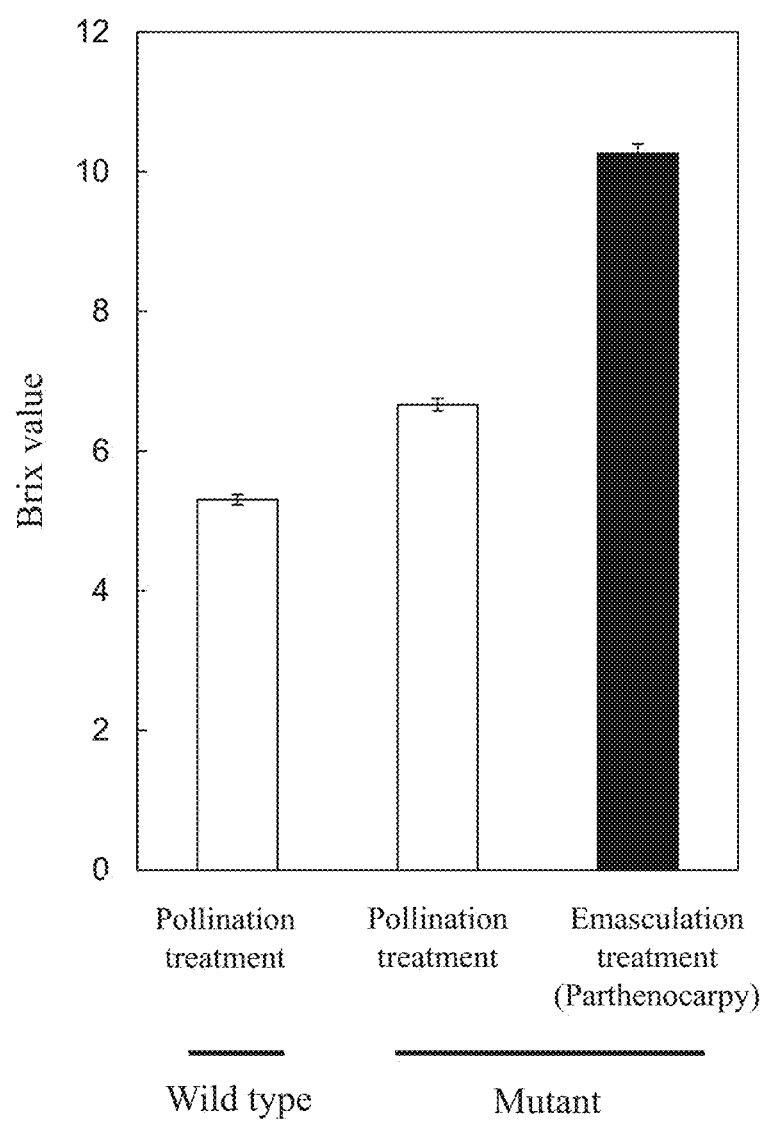
FIG. 5 shows the Brix value (sugar content index) of fruits for wild type and mutant tomato plants.

The mean of the Brix value as the sugar content index was 5.3% for fruits of the wild type strain subjected to pollination treatment (fruits with seeds/pollinated fruits) and 6.7% for fruits of the mutant strain subjected to pollination treatment, while the same significantly increased to 10.3% for fruits of the mutant strain subjected to emasculation treatment (parthenocarpic fruits) (FIG. 5). There was a significant difference at p<0.001 by the Tukey-kramer HSD test between the Brix values of the parthenocarpic fruits of the mutant strain and the fruits of the wild type and mutant strains subjected to pollination treatment (fruits with seeds/pollinated fruits). In addition, there was also a significant difference at p<0.001 by the Tukey-kramer HSD test between the Brix values of the fruits of the wild type strain subjected to pollination treatment and the fruits of the mutant strain subjected to pollination treatment. As described above, both fruits with seeds obtained by pollination treatment and seedless fruits obtained by emasculation treatment (parthenocarpic fruits) of the mutant strain had higher sugar contents than those of the wild type strain, indicating that the mutant strain produces high sugar-content fruits (FIG. 5).

The above results revealed that the parthenocarpic tomato mutant strain (mutant) obtained in Example 1 is a tomato mutant that has an improved sugar content in fruit as well as parthenocarpy.

Figure 6:
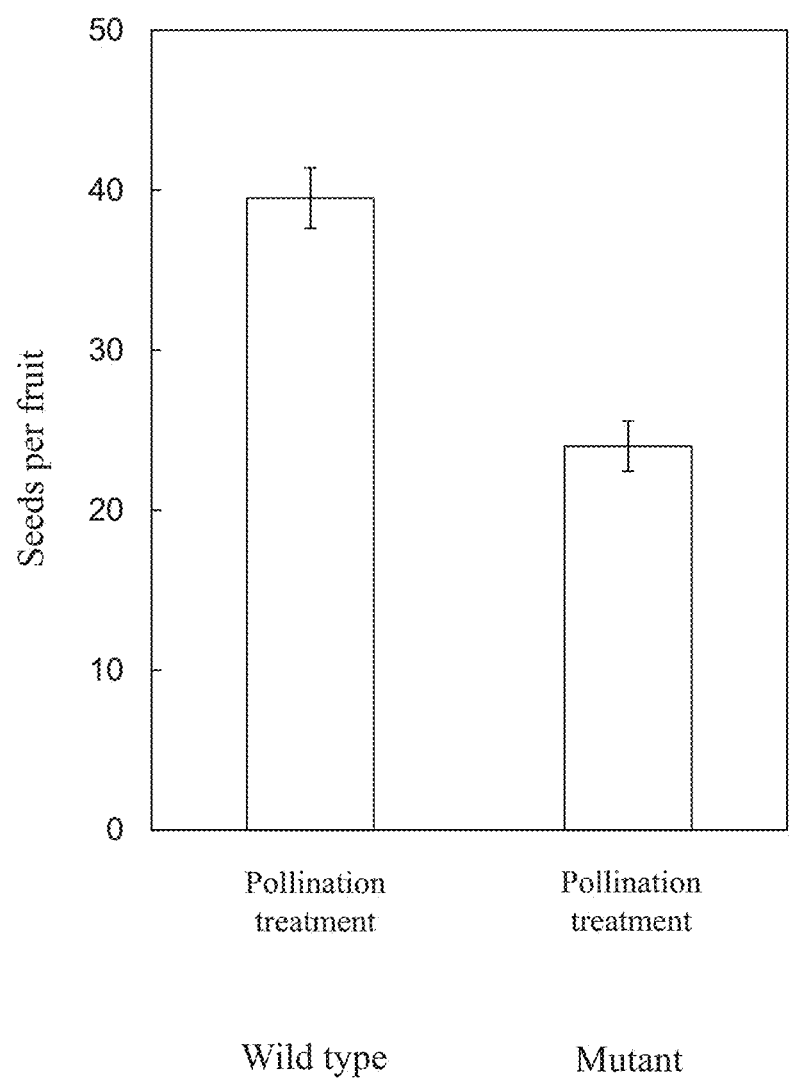
FIG. 6 shows the seed productivity for wild type and mutant tomato plants.

In addition, the wild type strain subjected to pollination treatment formed 40 seeds on average per fruit, and the mutant strain subjected to pollination treatment formed 24 seeds on average per fruit (FIG. 6). The number of seeds collected from the mutant strains is greater than half of that of the wild type strain, indicating that the mutant strain has no problem in the seed productivity required for breeding.

[Example 4] Identification of Causative Gene that Induces Parthenocarpy and Improves Sugar Content in the Mutant Strain (1) Analysis of Hereditary Nature in the Parthenocarpic Tomato Mutant Strain (Mutant)

The parthenocarpic tomato mutant strain (E8986 strain; mutant) selected in Example 1 was crossed with the wild type tomato variety Micro-Tom (wild type), and the thus formed $F_1$ seeds were collected. The $F_1$ seeds were sown and cultivated. After flowering, self-pollination was carried out, and the thus formed $F_2$ seeds were collected. The $F_2$ seeds were sown and cultivated. Specifically, seeds after water absorption for 3 days were sown in connected pots each containing culture soil and cultivated in a glass greenhouse. After flowering, fruit-setting was promoted by vibration pollination conducted using a vibrator. Seeds were collected from the obtained fruits.

The obtained $F_1$ seeds and $F_2$ seeds were examined for the segregation ratio between wild type phenotype and mutant phenotype based on differences in leaf morphology of tomato plants grown from the respective seeds (fusion of folioles for mutant leaves).

As a result, the segregation ratio between the wild type phenotype and the mutant phenotype was 6:0 in the $F_1$ population, and 77:30 in the $F_2$ population. The $\chi^2$ test was conducted and the results showed that the segregation rate in the $F_2$ population is highly likely to match an expected segregation rate of 3:1 (under the null hypothesis of the segregation rate being 3:1, the $\chi_2$ value is 0.53 with p value of 0.47), indicating that the causative gene (causative mutation) that imparts mutant phenotype is single recessive.

[Example 5] Rough Mapping of Causative Gene

Rough mapping of the causative gene on the tomato genome was conducted based on the results of Example 4. First, the parthenocarpic tomato mutant strain (mutant) selected in Example 1 was crossed with *Solanum pimpinellifolium*, which is a closely related species to tomato. The thus formed $F_1$ seeds were collected. The $F_1$ seeds were sown and cultivated. After flowering, self-pollination was carried out, and the thus formed $F_2$ seeds were collected. The $F_2$ seeds were sown and cultivated. Specifically, seeds after water absorption for 3 days were sown in connected pots each containing culture soil and cultivated in a glass greenhouse. From the obtained $F_2$ population, 22 individuals having the mutant phenotype (leaves with fused folioles) were selected.

Three folioles were collected from each of the selected 22 individuals for DNA extraction. The collected folioles were frozen using liquid nitrogen and the folioles were crushed using a micropestle. DNA was extracted from the crushed folioles using the Maxwell® 16 Tissue DNA Purification Kit (Promega) and an automated DNA purification instrument (Maxwell® 16 Instrument, Promega). The extracted DNA was used for polymorphism analysis based on the Solanaceae Coordinated Agricultural Project (SolCAP). Based on the results of SolCAP analysis, the gene frequency of the mutant-derived causative gene was calculated and a chromosome locus where the causative gene was positioned was narrowed down. There was a region with a high gene frequency of 0.87 to 0.93 for the mutant-derived causative gene in a region of about 77.4 Mb (77351578 bp) to 79.8 Mb (79847862 bp) (about 4.3 Mb) on the tomato chromosome 1. Therefore, the causative gene was considered to be positioned in that region.

[Example 6] Identification of Causative Gene Based on Genome Analysis (1) Mutation Identification by Genome Analysis As described in Example 4, the parthenocarpic tomato mutant strain (mutant) selected in Example 1 was crossed with the wild type tomato variety Micro-Tom (wild type), the obtained $F_1$ seeds were cultivated and self-pollinated, and the thus obtained $F_2$ seeds were sown and cultivated. 29 individuals showing the mutant phenotype (leaves with fused folioles) were selected. Three folioles were collected from each of these 29 individuals. DNA extraction from folioles was conducted in the same manner as in Example 5. After DNA extraction, one-tenth (1/10) volume of 3M sodium acetate and 2.5-times volume of 99.5% ethanol, and one-hundredth (1/100) volume of Ethachinmate (Nippon Gene Co., Ltd., Japan) were added for ethanol precipitation. After ethanol precipitation, DNA was washed with the addition of 70% ethanol, and a DNA solution was prepared with sterile water. After ethanol precipitation, equal amounts of DNAs of the respective individuals were mixed to form bulk DNA and next-generation sequence analysis was conducted therefor by a sequencer Illumina HiSeq 2000. The obtained nucleotide sequence was aligned with the wild type reference sequence, thereby identifying mutations.

Figure 7:
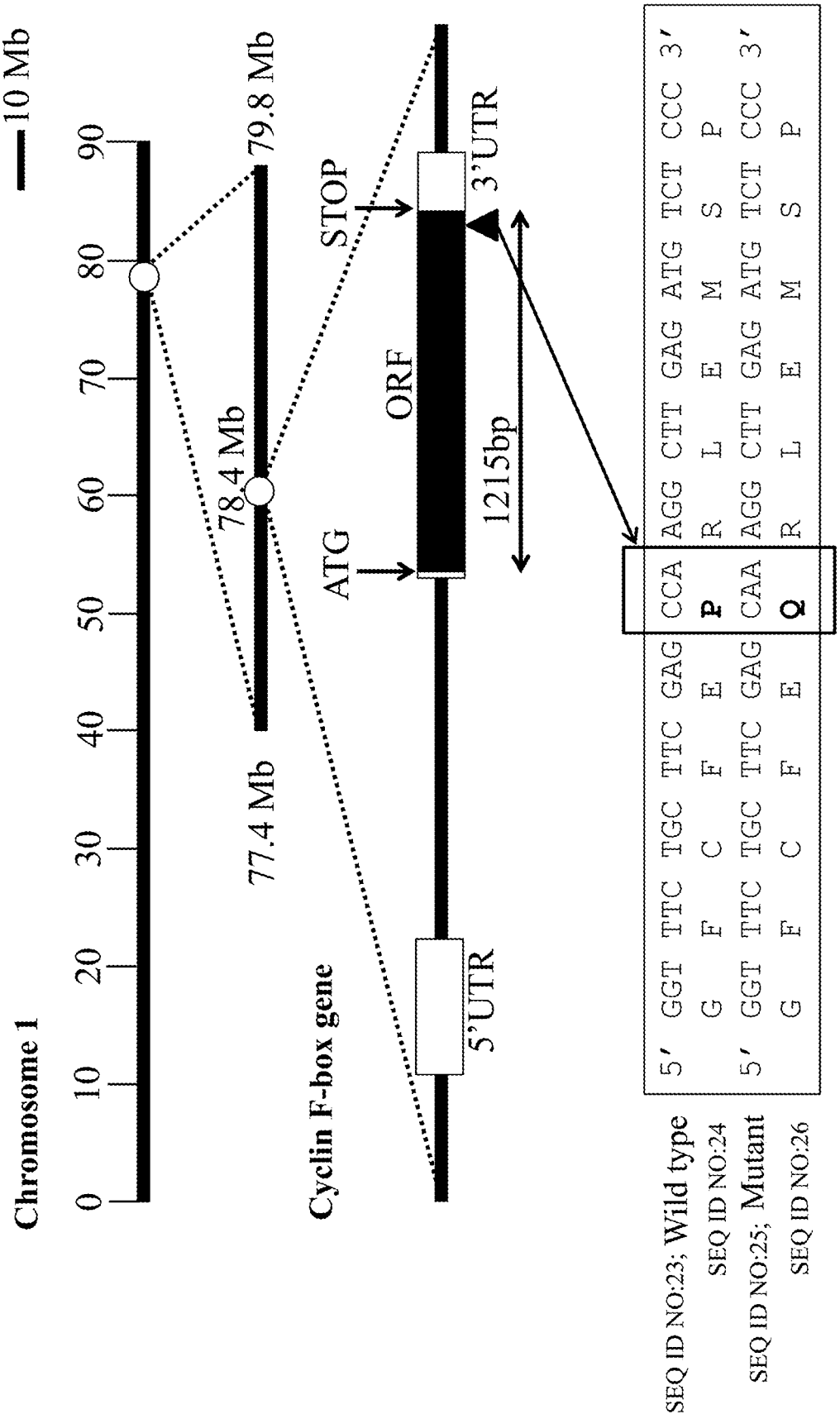
FIG. 7 schematically shows genome mapping of the causative gene in the mutant tomato plant.

As a result, the number of mutations generated in the region of about 77.4 Mb (77351578 bp) to 79.8 Mb (79847862 bp) of chromosome 1 was 186. Among the mutations, there was one mutation found in the translated regions (185 mutations in the untranslated regions) and the gene locus where the one mutation was present was found to encode the cyclin F-box protein which is an F-box family protein (FIG. 7). The mutation in the cyclin F-box gene was a missense mutation, in which codon CCA is mutated to CAA (nucleotide substitution of cytosine with adenine) to change an amino acid from proline to glutamine (FIG. 7). Since proline is a hydrophobic amino acid while glutamine is a hydrophilic amino acid, the amino acid mutation is considered to cause a change in conformation of the cyclin F-box protein. The above results suggested that this mutation in the cyclin F-box gene resulted in mutant phenotype (e.g., leaves with fused folioles, parthenocarpy, and high sugar content).

The nucleotide sequence (CDS sequence) encoding the cyclin F-box protein of the mutant tomato obtained by the above-described sequence analysis is set forth in SEQ ID NO: 3, and the amino acid sequence encoded by the nucleotide sequence is set forth in SEQ ID NO: 4. In addition, the nucleotide sequence (CDS sequence) encoding the cyclin F-box protein of the wild type tomato variety Micro-Tom is set forth in SEQ ID NO: 1, and the amino acid sequence encoded by the nucleotide sequence is set forth in SEQ ID NO: 2. The above-described mutation site (C→A) in the tomato cyclin F-box gene corresponds to the nucleotide at position 1193 of SEQ ID NOs: 1 and 3. In addition, the mutation site corresponds to the amino acid at position 398 in the amino acid sequences set forth in SEQ ID NOs: 2 and 4.

(2) Genotyping Using dCAPS Markers

As described in Example 4, the parthenocarpic tomato mutant strain (mutant) selected in Example 1 was crossed with the wild type tomato variety Micro-Tom (wild type), the obtained $F_1$ seeds were cultivated and self-pollinated, and the thus obtained $F_2$ seeds were sown and cultivated. 128 $F_2$ individuals ($F_2$ population) were obtained. Wild type and mutant phenotypes were distinguished for 128 individuals based on the differences in leaf morphology. As a result, 104 individuals showed the wild type phenotype (without fusion of folioles) and 24 individuals showed the mutant phenotype (with fusion of folioles). Three folioles were collected from each of all the 128 $F_2$ individuals. DNA extraction from folioles was conducted in the same manner as in Example 5.

Next, PCR was conducted using the extracted DNA as a template and dCAPS primers, thereby amplifying a region including the mutation site in the cyclin F-box gene. The composition of a PCR reaction solution contained 12. μL it of 2× Go Taq® GreenMaster Mix (Promega), 2.5 μL each of 10 μM primers, 6.5 μL of sterile water, and 1 μL of template DNA (25 μL in total). The dCAPS primers were designed such that a PCR product for the wild type strain was exclusively digested with the restriction enzyme NcoI while a PCR product for the mutant strain was not digested therewith. The nucleotide sequences of dCAPS primers (dCAPS markers) used were as follows: forward primer: 5'-CCCGCATGCCACACAAGTATTT-3' (SEQ ID NO: 5) and reverse primer: 5'-ATCACATATCAGGGAGACATCT-CAAGCCAT-3' (SEQ ID NO: 6). PCR reaction conditions were thermal denaturation at 95° C. for 2 minutes, followed by 35 cycles at 95° C. for 30 seconds, 56° C. for 1 minute, and 72° C. for 2 minutes; and then at 72° C. for 7 minutes. After PCR, 0.5 μL of the restriction enzyme NcoI was added to 10 μL of the PCR product, and the mixture was allowed to stand at 37° C. for 16 hours for digestion of DNA. The digested DNA sample was incubated at 70° C. for 15 minutes, thereby inactivating the restriction enzyme. Thereafter, the DNA sample was subjected to electrophoresis using 1.5% agarose gel. As a control, DNA extracted from folioles of the wild type tomato variety Micro-Tom was tested in the same manner.

Figure 8:
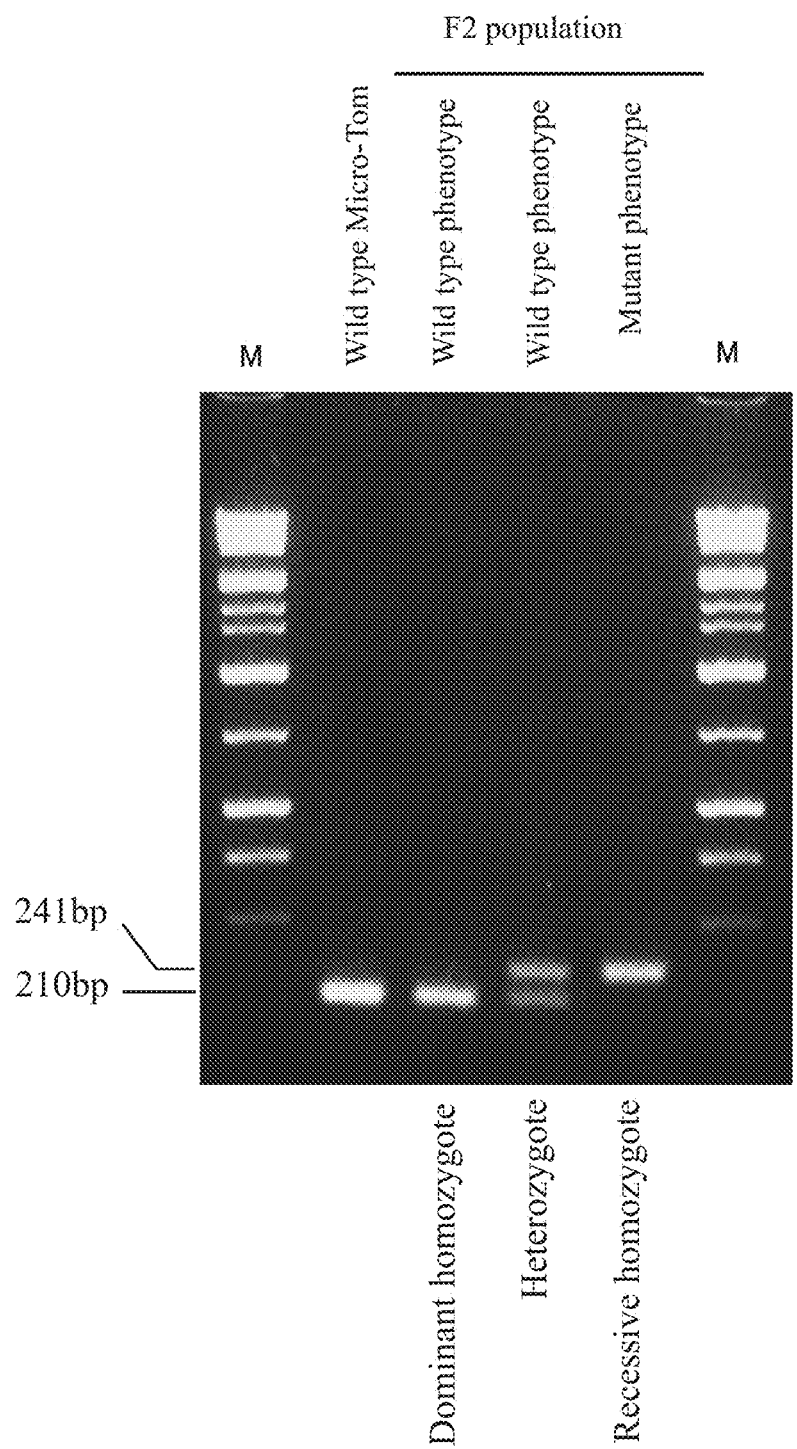
FIG. 8 shows the results of genotyping using dCAPS markers. In the figure, M denotes a DNA molecular weight marker (Gene Ladder Wide 1).

FIG. 8 shows the results. Bands of the nucleic acid fragment (241 bp) amplified with the forward and reverse primers and the NcoI-cleaved fragment thereof (210 bp) were observed. Although 104 individuals of $F_2$, which exhibited the wild type phenotype, had band(s) indicating a dominant homozygote or heterozygote (38 dominant homozygous individuals and 66 dominant heterozygous individuals), all of 24 individuals of $F_2$, which exhibited the mutant phenotype, had a band indicating a recessive homozygote (FIG. 8, Table 1). It was also shown that the segregation ratio for 128 individuals of $F_2$ based on the results is highly likely to match an expected segregation ratio of 1:2:1 (Table 1). Since the phenotype completely matches the genotype, it was suggested that the cyclin F-box gene is highly likely to be the causative gene. This supported that the above-described parthenocarpy-inducing mutation in the cyclin F-box gene caused the characteristic phenotype in the mutant strain. In addition, it was shown that the dCAPS markers used above can also be used as linkage markers of the causative gene.

TABLE 1

| | Phenotype of $F_2$ population | | | | | | | |
|---|---|---|---|---|---|---|---|---|
| | Wild type Genotype | | | Mutant Genotype | | | Expected | |
| Parents for Crossing | W/W | W/m | m/m | W/W | W/m | m/m | segregation ratio (W/W:W/m:m/m) | $\chi^2$ value | P value |
| Wild type × Mutant | 38 | 66 | 0 | 0 | 0 | 24 | 1:2:1 | 3.19 | 0.20 |

W/W, Dominant homozygote;
W/m, heterozygote;
m/m, recessive heterozygote.

[Example 7] Sequence Analysis of the Cyclin F-Box Gene of Commercial Varieties

The nucleotide sequence of the cyclin F-box gene was analyzed for the parthenocarpic tomato mutant strain selected in Example 1 (E8986 strain; mutant) (hereinafter also referred to as mutant Micro-Tom); the wild type tomato variety Micro-Tom (hereinafter also referred to as wild type Micro-Tom); and 9 tomato commercial varieties: "Aichi First," "House Momotaro," "Zuiko 102," "Reiyou," "Reika," "Ailsa Craig," "Money maker," "M82," and "Levanzo."

Seeds after water absorption for 3 days were sown in connected pots (Shinwa Co., Ltd.) each containing culture soil (Jiffy Mix, Sakata Seed Corporation) as cultivation containers and cultivated in a glass greenhouse. Three folioles were collected from each strain or variety, frozen with liquid nitrogen, and crushed using a micropestle. After crushing, DNA was extracted therefrom using the Maxwell® 16 Tissue DNA Purification Kit (Promega) and an automated DNA purification instrument (Maxwell® 16 Instrument, Promega). After DNA extraction, a region including the mutation site in the cyclin F-box gene was amplified by PCR. The composition of a PCR reaction solution contained 1 μL of DNA template, 5 μL of KOD-Plus Neo buffer, 5 μL of 25 mM dNTPs, 3 μL of 2 mM $MgSO_4$, 1.5 μL each of 10 μM primers, 32 μL of sterile water, and 1.0 μL of KOD Plus Neo (50 μL in total). The nucleotide sequences of the primers used for PCR were as follows: forward primer: 5'-GGAAACCAGACCGTCCTGAC-3' (SEQ ID NO: 7); and reverse primer: 5'-TGCATTGAGAG-GAGCTAGGG-3' (SEQ ID NO: 8). PCR reaction conditions were thermal denaturation at 94° C. for 2 minutes, followed by 45 cycles at 98° C. for 10 seconds, 57° C. for 30 seconds, and 68° C. for 1 minute. Thereafter, the PCR reaction solution was subjected to electrophoresis with 1.5% agarose gel, and DNA of about 400 bp was excised and collected from agarose gel. A FastGene Gel/PCR Extraction Kit (Nippon Genetics Co., Ltd.) was used for collecting DNA from agarose gel. After collection of DNA, sequencing was conducted. The sequencing solution was prepared by mixing 100 ng of template DNA, 3.75 μL of sequencing buffer, 1 μL of 3.2 pmol primer, and 0.5 μL of Big Dye and filled up to 20 μL with sterile water. The primer used was the above-described forward primer of SEQ ID NO: 7. After the reaction, DNA was purified using a BigDye XTerminator® Purification Kit (Applied Biosystems) and sequence analysis was performed using a genetic analyzer Applied Biosystems® 3500xL.

Figure 9:
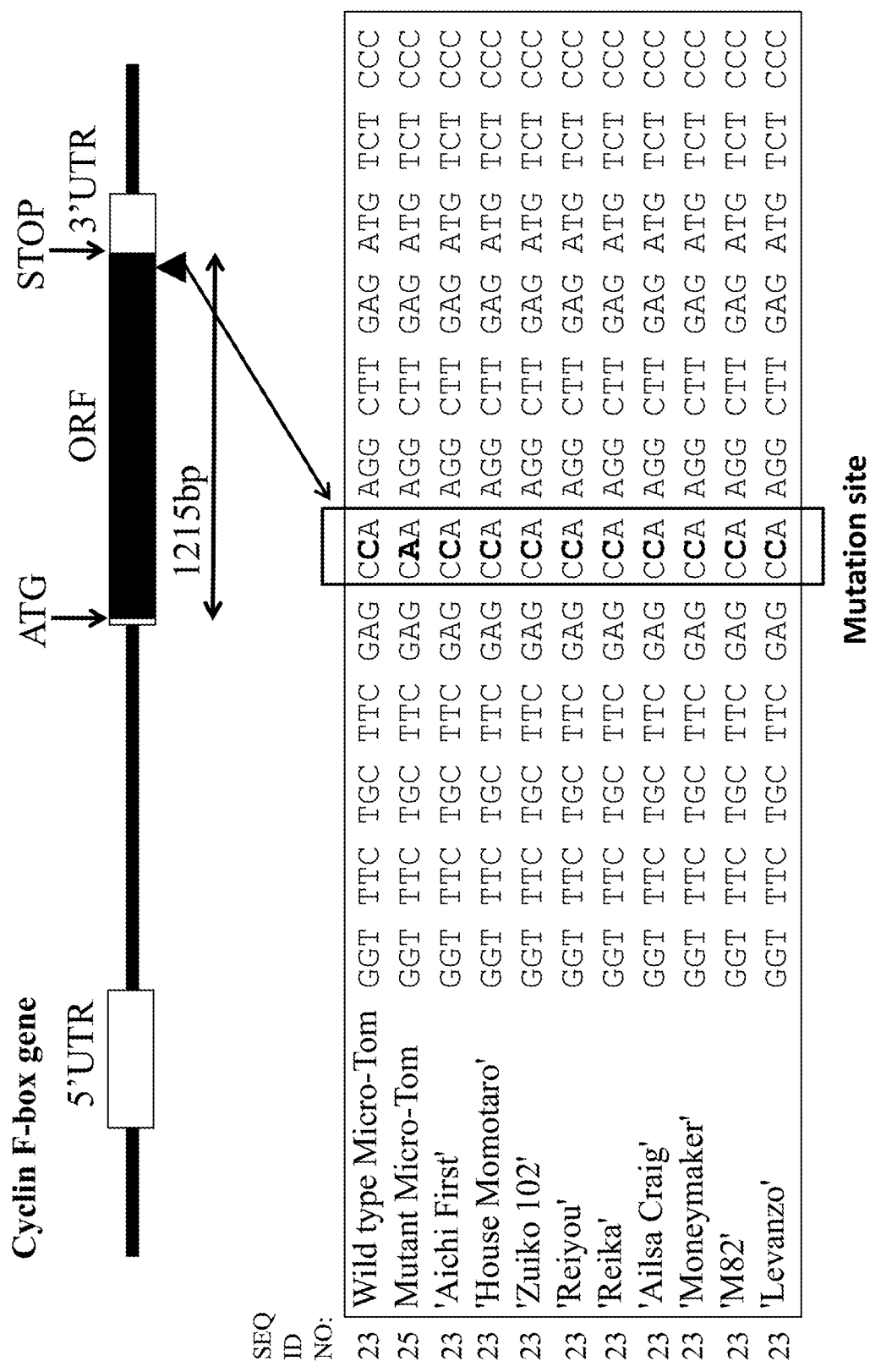
FIG. 9 shows the nucleotide sequences comprising sites corresponding to the mutation and their surrounding regions in various tomato varieties.

As a result, a comparison of the analyzed sequence of the wild type Micro-Tom and that of the mutant Micro-Tom confirmed that CCA in the nucleotide sequence of the wild type Micro-Tom was mutated to CAA in the nucleotide sequence of the mutant Micro-Tom, as in the case of Example 6. In addition, the analyzed sequence of each of the commercial varieties was found to be identical to the analyzed sequence of the wild type Micro-Tom. In other words, the nucleotide sequence of a site corresponding to the mutation was CAA in all of the commercial varieties. FIG. 9 summarizes the results. The analyzed sequence of the wild type Micro-Tom and the commercial varieties is set forth in SEQ ID NO: 9, and the analyzed sequence of the mutant Micro-Tom is set forth in SEQ ID NO: 10.

The above results confirmed that the above-described parthenocarpic mutation found in the cyclin F-box gene of the mutant Micro-Tom is a mutation induced by EMS treatment. Since the analyzed sequence of the commercial varieties was 100% identical to the analyzed sequence of the wild type Micro-Tom, it was further shown that the above-described parthenocarpy-inducing mutation can be introduced into other tomato varieties.

[Example 8] Obtainment of the Cyclin F-Box Gene Mutant

M2 seeds of about 9,000 tomato EMS-mutagenized strains produced in the same manner as in Example 1 were sown at 10 seeds each on culture soil and cultivated. DNA was collectively extracted from a group of grown plant individuals per each strain by conventional methods. Extracted DNA (M2 DNA) was divided into a 96-well plate and stored at −20° C. Next, M2 DNAs of 8 strains each were combined and divided into a new 96-well plate to prepare DNA pools. The prepared DNA pools from about 9,000 strains were used for selection of mutants by Targeting Induced Local Lesions IN Genomes (TILLING). Selection of mutants by TILLING was conducted basically in accordance with the method described in Okabe et al. (2011) Plant and Cell Physiology 52: 1994-2005, thereby selecting a strain having a mutation in the cyclin F-box gene (Solyc01g095370). Specifically, PCR was conducted using cyclin F-box gene-specific forward and reverse primers, which were 5'-labeled with different fluorescent dyes, and DNA from the above-described DNA pools as a template, to amplify a target region in the cyclin F-box gene. Table 2 indicates the cyclin F-box gene-specific forward and reverse primers used herein.

TABLE 2

| Primer name | Sequence (5'-3') | Remarks |
|---|---|---|
| F-box-TILL1-2-Fw | ccacagccttagggttggag (SEQ ID NO: 11) | 5'-end, Dy-681 fluorescent label |
| F-box-TILL1-2-Rev | acggtctggtttcccaatcc (SEQ ID NO: 12) | 5'-end, Dy-781 fluorescent label |
| F-box-TILL2-2-Fw | gcattggctatctgtgcaaaca (SEQ ID NO: 13) | 5'-end, Dy-681 fluorescent label |
| F-box-TILL2-2-Rev | agacaacttgtccctgtcttgg (SEQ ID NO: 14) | 5'-end, Dy-781 fluorescent label |

Then, the obtained PCR product was heated and cooled for promoting formation of a heteroduplex. Next, the heated and cooled nucleic acids were treated with a recombinant SlENDO1 nuclease to cleave a nucleotide mismatch site in the formed heteroduplex. The recombinant SlENDO1 nuclease was extracted and purified from a SlENDO1-overexpressing transgenic tomato, into which the pGWB8 binary vector (Nakagawa et al. (2007) J. Biosci. Bioeng., 104: 34-41) containing the cloned SlENDO1 nuclease gene (accession no. AB667996) had been introduced. Nucleic acids treated with the recombinant SlENDO1 nuclease were subjected to polyacrylamide gel electrophoresis (PAGE). If a cleavage fragment was observed, it was considered that there was a mutation. Thus, strains suggested to have the mutation was selected. As a secondary screening, TILLING was conducted for each strain in the DNA pool including the strains suggested to have the mutation to select a mutated strain. The mutation was identified by sequence analysis.

M3 seeds of the selected strains were sown at 20 seeds each on culture soil and cultivated. Among the grown plant individuals, individuals having the mutation homozygously were selected by genotyping using TILLING. Specifically, DNA was extracted from each of the plant individuals by conventional methods. Then, two types of template nucleic acid samples, i.e., a PCR template used for detection of heterozygote comprising DNA of the plant individual alone, and a PCR template used for detection of homozygote/heterozygote in which DNA of the plant individual is combined with the wild type DNA were prepared, and subjected to genotyping. A target region in the cyclin F-box gene was amplified by PCR in the above-mentioned manner, and the obtained PCR product was heated and cooled to promote formation of a heteroduplex. The resulting product was cleaved at the nucleotide mismatch site in the heteroduplex with the recombinant SlENDO1 nuclease, and then subjected to polyacrylamide gel electrophoresis (PAGE) and the presence or absence of a cleavage fragment was observed. If a cleavage fragment was found only in the case of using the above PCR template in which DNA of the plant individual is combined with the wild type DNA and a cleaved fragment was not found in the case of using the above PCR template comprising DNA of the plant individual alone, the genotype of the test strain was determined to be homozygous. The nucleotide sequence of the amplified region of the cyclin F-box gene in the mutant strain determined to be homozygous was determined and compared with the nucleotide sequence of the corresponding region in the cyclin F-box gene (SEQ ID NO: 1) of the wild type strain, thereby identifying a genetic mutation.

dCAPS primers were designed in view of the identified genetic mutation so that they yield amplification products which were characterized in that a PCR product obtained in the wild type strain was digested with a particular restriction enzyme recognizing the mutation site while a PCR product obtained in a mutant strain was not digested with the same restriction enzyme. The cyclin F-box gene of the mutant strain was amplified using the dCAPS primers and cleaved with a restriction enzyme recognizing the mutation site, to confirm the genetic mutation and genotype. Fruit-setting was induced in plant individuals (M3) confirmed to be homozygous mutants in the same manner as in Example 3 and the Brix values (sugar contents) of the resulting fruits (red ripe fruits) were determined using a portable refractometer N-20E (ATAGO). Seeds (M4 seeds) were collected from the homozygous mutant individuals.

As a result, two strains, each of which had a missense mutation in the cyclin F-box gene and showed a high sugar content in the M3 generation, were isolated. These mutant strains, W283 and W3583 strains, had a nucleotide substitution in the nucleotide sequence of the cyclin F-box gene, which causes a non-conservative amino acid substitution. Specifically, W283 strain had a mutation that causes a substitution of glycine at position 301 in the cyclin F-box protein (SEQ ID NO: 2) by arginine (a substitution of guanine at position 901 of the nucleotide sequence of SEQ ID NO: 1 by adenine). W3583 strain had a mutation that causes a substitution of serine at position 37 in the cyclin F-box protein (SEQ ID NO: 2) by leucine (a substitution of cytosine at position 110 in the nucleotide sequence of SEQ ID NO: 1 by thymine).

The dCAPS primers used for confirmation of the genetic mutations and genotypes of W283 and W3583 strains were as described below.

TABLE 3

| Primer name | Sequence (5'-3') | Mutation site-recognizing enzyme |
|---|---|---|
| W283-dCAPS-Fw | ttctggaacaatgaagtggttg (SEQ ID NO: 15) | BsaXI |
| W283-dCAPS-BsaXI-Rev | ccttaattatgtcaggacggtct ggtttcacaatcc (SEQ ID NO: 16) | |
| W3583-dCAPS-XspI-Fw | ttcattttcagagcttaatgatg aagaaaatagagaggcttccc (SEQ ID NO: 17) | XspI |
| W3583-dCAPS-Rev | tgaatgcaagggaggtcaatact (SEQ ID NO: 18) | |

Figure 10:
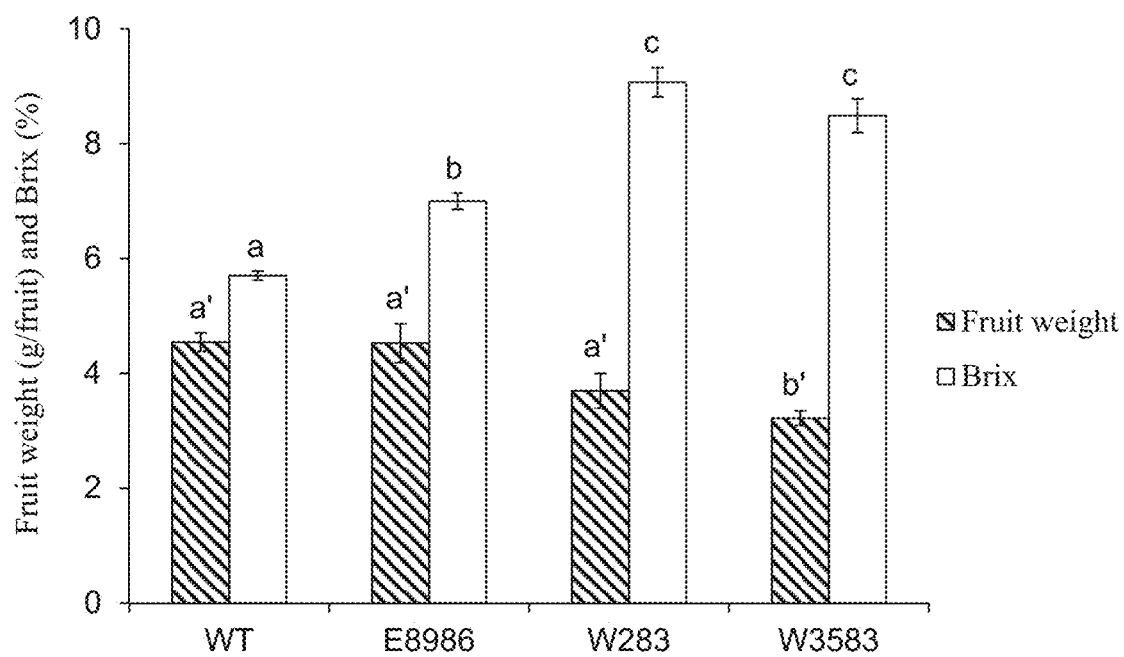
FIG. 10 shows the fruit weights (g/fruit) and the Brix values (%) of red ripe fruits obtained via pollination treatment of wild type and mutant tomato plants. A significant difference was tested with the Tukey-Kramer HSD test (p<0.01). The difference between alphabets on bars indicates the presence of a significant difference (p<0.01).

Brix values (sugar contents) were measured for pollinated fruits (red ripe fruits) of W283 and W3583 strains and compared with the Brix values measured in the same manner for pollinated fruits (red ripe fruits) of the wild type and pollinated fruits (red ripe fruits) of E8986 strain obtained in Example 1. Table 4 and FIG. 10 show the comparison results. Table 4 and FIG. 10 also show the mean weight per fruit of pollinated fruits obtained for each strain.

TABLE 4

|  | Wild type (WT) | E8986 | W283 | W3583 |
|---|---|---|---|---|
| Brix value* | 5.7 ± 0.1 | 7.0 ± 0.1 | 9.1 ± 0.3 | 8.5 ± 0.3 |
| Fruit weight (g/fruit)* | 4.5 ± 0.2 | 4.5 ± 0.3 | 3.7 ± 0.3 | 3.2 ± 0.1 |

*Mean ± Standard error (SE)

The W283 and W3583 strains had higher sugar contents than that of the wild type strain, and their high sugar contents were also greater than the sugar content of the E8986 strain. The E8986 strain also had a higher sugar content than that of the wild type strain. The results showed that a non-conservative substitution in the cyclin F-box protein is capable of increasing (improving) the sugar content in fruit.

Figure 11:
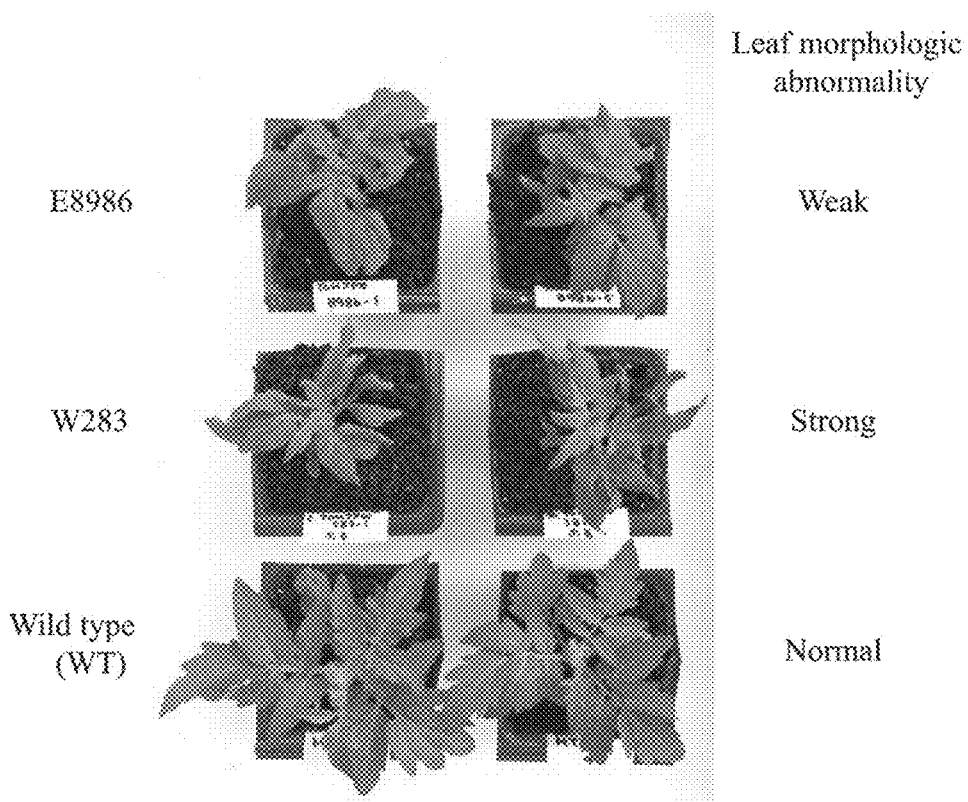
FIG. 11 is a photograph showing the influence of the cyclin F-box gene mutation on growth. The E8986 strain in the upper panels exhibited abnormal leaf morphology (relatively weak abnormality), while the W283 strain in the middle panels showed a stronger leaf morphologic abnormality compared with the E8986 strain. The wild type leaf morphology shown in the lower panels is normal.

Additionally, the W283 strain had particularly characteristic leaf morphology and exhibited a leaf morphologic abnormality stronger than the abnormality of the E8986 strain (FIG. 11). In contrast, the W3583 strain exhibited a leaf morphologic abnormality at a relatively weak level and had no parthenocarpy (parthenocarpic rate of 0%).

The nucleotide sequences of the mutant cyclin F-box genes of the W3583 and W283 strains are set forth in SEQ ID NOs: 19 and 21, respectively, and the amino acid sequences of the mutant cyclin F-box proteins encoded by the sequences are set forth in SEQ ID NOs: 20 and 22, respectively.

INDUSTRIAL APPLICABILITY

The plant (e.g., tomato) according to the present invention can be used for easily and stably producing high-sugar content fruits without the need for special cultivation methods and facilities for achieving high sugar content in fruits. The plant according to the present invention can also be used as a breeding material for producing a parthenocarpic plant or a high-sugar content fruit-producing plant. Reduction of fruit yields or quality deterioration in the cultivation during the summer and winter can be prevented with the use of the parthenocarpic plant according to the present invention, thereby making it possible to produce high-quality fruits throughout a year.

All publications, patents and patent applications cited in the present description are incorporated herein by reference in their entirety.

SEQUENCE LISTING FREE TEXT

SEQ ID NO: 1: CDS sequence encoding the wild type cyclin F-box protein

SEQ ID NO: 2: Amino acid sequence of the wild type cyclin F-box protein

SEQ ID NO: 3: CDS sequence encoding the mutant cyclin F-box protein (from E8986)

SEQ ID NO: 4: Amino acid sequence of the mutant cyclin F-box protein (from E8986)

SEQ ID NOs: 5 to 8: Primers SEQ ID NO: 9: Analyzed sequence of the wild type Micro-Tom SEQ ID NO: 10: Analyzed sequence of the mutant Micro-Tom (E8986)

SEQ ID NOs: 11 to 18: Primers SEQ ID NO: 19: CDS sequence encoding the mutant cyclin F-box protein (from W3583)

SEQ ID NO: 20: Amino acid sequence of the mutant cyclin F-box protein (from W3583)

SEQ ID NO: 21: CDS sequence encoding of the mutant cyclin F-box protein (from W283)

SEQ ID NO: 22: Amino acid sequence of the mutant cyclin F-box protein (from W283)

What is claimed is:

1. A parthenocarpic tomato plant having a mutant cyclin F-box gene comprising a nucleotide mutation that causes a non-conservative amino acid substitution of proline at position 398 defined based on the amino acid sequence set forth in SEQ ID NO: 2 in a cyclin F-box protein.

2. The plant according to claim 1, wherein the plant has an improved sugar content in fruit.

3. The plant according to claim 1, wherein the non-conservative amino acid substitution of proline is a substitution of proline by glutamine.

4. The plant according to claim 1, wherein the plant is a seed or fruit.

5. A method for producing a parthenocarpic tomato plant having an improved sugar content in fruit, comprising introducing a nucleotide mutation that causes a non-conservative amino acid substitution of proline at position 398 defined based on the amino acid sequence set forth in SEQ ID NO: 2 in a cyclin F-box protein, into a cyclin F-box gene of a tomato plant.

6. The method according to claim 5, wherein the non-conservative amino acid substitution of proline is a substitution of proline by glutamine.

7. A method of tomato plant breeding, comprising:
crossing tomato plants using the plant according to claim 1 as a breeding parent,
obtaining progeny plants, and
selecting a progeny tomato plant having said mutant cyclin F-box gene introduced thereinto.

8. The method according to claim 7, wherein the progeny tomato plant is selected by detecting the mutant cyclin F-box gene in the progeny tomato plant.

9. A method for screening for a tomato plant having an improved sugar content in fruit, comprising:
introducing a nucleotide mutation that causes a non-conservative amino acid substitution into a cyclin F-box gene of a tomato plant, and
selecting a plant having an improved sugar content in fruit as compared with wild type plant.

* * * * *

UNITED STATES PATENT AND TRADEMARK OFFICE
CERTIFICATE OF CORRECTION

PATENT NO.        : 10,745,710 B2                                    Page 1 of 1
APPLICATION NO.   : 15/750386
DATED             : August 18, 2020
INVENTOR(S)       : Hiroshi Ezura et al.

It is certified that error appears in the above-identified patent and that said Letters Patent is hereby corrected as shown below:

On the Title Page

Item [73], Delete "Igaraki (JP)" and insert --Ibaraki (JP)--

Signed and Sealed this
Eighth Day of December, 2020

Andrei Iancu
*Director of the United States Patent and Trademark Office*